US012728022B2

(12) United States Patent
Souply et al.

(10) Patent No.: US 12,728,022 B2
(45) Date of Patent: Sep. 8, 2026

(54) COVERING SHELL FOR A PROSTHESIS AND LIMB PROSTHESIS

(71) Applicant: CHABLOZ ORTHOPÉDIE, Seyssinet-Pariset (FR)

(72) Inventors: Marc Souply, Vizille (FR); Anousak Khounlavong, Seyssinet-Pariset (FR); Elodie Ronayette-Lamoine, Grenoble (FR); Jules Revais, Seyssinet-Pariset (FR)

(73) Assignee: CHABLOZ ORTHOPÉDIE, Seyssinet-Pariset (FR)

( * ) Notice: Subject to any disclaimer, the term of this patent is extended or adjusted under 35 U.S.C. 154(b) by 1071 days.

(21) Appl. No.: 17/881,523

(22) Filed: Aug. 4, 2022

(65) Prior Publication Data

US 2022/0387195 A1 Dec. 8, 2022

Related U.S. Application Data

(63) Continuation-in-part of application No. PCT/FR2021/050248, filed on Feb. 11, 2021, and a (Continued)

(30) Foreign Application Priority Data

Feb. 19, 2020 (FR) ....................................... 2001627
Feb. 19, 2020 (FR) ....................................... 2001628

(51) Int. Cl.
*A61F 2/54* (2006.01)
*A61F 2/50* (2006.01)
(Continued)

(52) U.S. Cl.
CPC .................. *A61F 2/66* (2013.01); *A61F 2/54* (2013.01); *A61F 2/583* (2013.01); (Continued)

(58) Field of Classification Search
CPC .... A61F 2/66; A61F 2/54; A61F 2/583; A61F 2/80; A61F 2002/5066; A61F 2002/5081; (Continued)

(56) References Cited

U.S. PATENT DOCUMENTS 10,130,496 B2 * 11/2018 Kampas ................ A61F 2/6607
10,172,276 B2 1/2019 Janssen et al.
(Continued)

FOREIGN PATENT DOCUMENTS

CN 1980616 A 6/2007
DE 322909 C 7/1920
(Continued)

OTHER PUBLICATIONS

Nicholas Herbert et al., “A preliminary investigation into the development of 3-D printing of prosthetic sockets,” J. Rehabil Res Dev., Mar./Apr. 2005, p. 141-146, vol. 42, No. 2.

*Primary Examiner* — Bruce E Snow
(74) *Attorney, Agent, or Firm* — H&I PARTNERS; Chai Im; C. Andrew Im

(57) ABSTRACT

A covering shell for a prosthesis of a given limb, the shell having at least two zones of different flexibility. The arrangement of the zones of the covering shell in relation to one another corresponding to the arrangement of the parts of the given limb having different hardnesses. An exoskeletal structure, having preferably a tubular shape, of a prosthesis of a given limb. The exoskeletal structure being designed to provide a connection between a socket and a hand prosthesis or between a socket and a foot prosthesis, in order to form the prosthesis of the limb. The exoskeletal structure having at least two zones of different flexibility. The arrangement of the zones of the exoskeletal structure in relation to one another corresponding to the arrangement of the parts of the given limb having different hardnesses.

8 Claims, 11 Drawing Sheets

Related U.S. Application Data continuation-in-part of application No. PCT/FR2021/050249, filed on Feb. 11, 2021.

(51) Int. Cl.

| | |
|---|---|
| ***A61F 2/58*** | (2006.01) |
| ***A61F 2/60*** | (2006.01) |
| ***A61F 2/66*** | (2006.01) |
| *A61F 2/80* | (2006.01) |

(52) U.S. Cl.

CPC ................. *A61F 2002/5001* (2013.01); *A61F 2002/5066* (2013.01); *A61F 2002/5081* (2013.01); *A61F 2002/5095* (2013.01); *A61F 2002/607* (2013.01); *A61F 2002/6614* (2013.01); *A61F 2/80* (2013.01)

(58) Field of Classification Search

CPC ........ A61F 2002/5095; A61F 2002/607; A61F 2002/6614; A61F 2002/5001

See application file for complete search history.

(56) References Cited

U.S. PATENT DOCUMENTS

| | | | | |
|---|---|---|---|---|
| 11,224,525 | B2 * | 1/2022 | Radspieler | A61F 2/7812 |
| 2006/0015192 | A1 | 1/2006 | Clausen et al. | |
| 2012/0283846 | A1 * | 11/2012 | Janssen | A61F 2/60 156/305 |
| 2018/0368996 | A1 | 12/2018 | Van Vliet et al. | |
| 2020/0038203 | A1 * | 2/2020 | Piller | A61F 2/50 |

FOREIGN PATENT DOCUMENTS

| | | | |
|---|---|---|---|
| EP | 2 944 290 | A1 | 11/2015 |
| KR | 20110034879 | A | 4/2011 |
| WO | 2017012888 | A1 | 1/2017 |

* cited by examiner

COVERING SHELL FOR A PROSTHESIS AND LIMB PROSTHESIS

RELATED APPLICATIONS

This application is a continuation-in-part application of international application PCT/FR2021/050249 filed Feb. 11, 2021, which claims priority from French application 2001627 filed Feb. 19, 2020, and this application is a continuation-in-part application of international application PCT/FR2021/050248 filed Feb. 11, 2021, which claims priority from French application 2001628 filed Feb. 19, 2022, each of which is incorporated herein by reference in its entirety.

TECHNICAL FIELD

The present invention relates to a covering shell for a prosthesis.

BACKGROUND OF THE INVENTION

Following a limb amputation, to recover their mobility, a patient is usually fitted with a prosthesis which will partially replace the functionality of the lost limb. The physical form of such a prosthesis is determined by the constraints imposed by the function thereof. For example, to obtain a leg replacement prosthesis, the prosthesis comprises a bar ending with a mechanical joint in order to take on leg functionality as well as possible. The physical appearance of the prosthesis remains of secondary importance.

In order to impart a similar aesthetic to the lost limb, a prosthesis can be provided with a covering shell. An example of such a shell is described by the document EP 2 944 290 A1. To obtain a natural appearance, the shell described by the document cited takes the shape of a leg. Furthermore, openings are provided to allow ventilation and to reduce the weight of the shell.

The shells known from the prior art only reproduce a replaced limb imperfectly.

The present invention further relates to an exoskeletal structure of a prosthesis of a given limb.

Following a limb amputation, to recover their mobility, a patient is usually fitted with a prosthesis which will partially replace the functionality of the lost limb. The physical form of such a prosthesis is determined by the constraints imposed by the function thereof. For example, to obtain a leg replacement prosthesis, the prosthesis known from the prior art comprises a bar ending with a mechanical joint in order to take on leg functionality as well as possible. In order to impart a similar aesthetic to the lost limb, such a prosthesis known from the prior art can be provided with a covering shell, also known from the prior art. An example of such a shell is described by the document EP 2 944 290 A1. To obtain a natural appearance, the shell described by the document cited takes the shape of a leg. Furthermore, openings are provided to allow ventilation and to reduce the weight of the shell.

The shells known from the prior art only reproduce a replaced limb imperfectly. The need to handle a prosthesis and a shell can prove to be cumbersome.

OBJECT AND SUMMARY OF THE INVENTION

The aim of the present invention is then that of providing a covering shell for a prosthesis of a given limb which reproduces the replaced limb more realistically.

The above aim is achieved by a shell which resembles, to the touch, the replaced limb. The shell of the present invention resembles through the flexibility thereof the different parts felt when touching the replaced limb.

In the preferred example, the covering shell for a prosthesis of a given limb comprises:

- at least two zones of different flexibility,
- the arrangement of said zones in relation to one another corresponding to the arrangement of parts of the given limb having different hardnesses.

The shell can also comprise a first zone which differs from a second zone in relation to:

- a thickness and/or
- a material and/or
- a three-dimensional pattern, in order to obtain a first zone having a different flexibility from a second zone.

The shell advantageously comprises

- a first zone has a lesser flexibility than a second zone, the first zone being arranged to coincide with a hard part of the limb, and/or
- a second zone has a greater flexibility (9.1, 9.2) than a first zone, the second zone being arranged to coincide with a soft part of the limb.

Preferably,

- the first zone and the second zone have different thicknesses, and
- the first zone and the second zone are obtained with a rib or with a recess.

The shell can also have a tubular shape capable of receiving said prosthesis inside the tubular shape.

Preferably,

- a flexibility of the shell remains mostly constant along a length of the tubular shape, and/or
- the flexibility of the shell mostly changes along a circumference of the tubular shape.

The shell can also be provided for a leg prosthesis, preferably for a tibia prosthesis or for an arm prosthesis.

Advantageously, the shell can have:

- a zone having a greater thickness than a mean thickness of the shell, the zone being located on the shell like the tibia is located under a leg's skin and/or
- a zone having a lesser thickness than a mean thickness of the shell, the zone being located on the shell like a muscle or a tendon is located under a leg's skin,
- the muscle or the tendon being preferably the soleus, the tibialis anterior, the fibularis longus, the extensor digitorum longus, the gastrocnemius or Achille's tendon.

Said shell can comprise a mostly smooth outer surface, the changes in thickness being located on an inner surface of the shell.

Said shell can also comprise:

- a material comprising a thermoplastic polyurethane (TPU) and/or
- a material comprising a polyamide.

Also described is an assembly of a covering shell, as mentioned above, for a leg prosthesis and a covering shell for a foot prosthesis, the covering shell of the leg prosthesis being integral with the covering shell of the foot prosthesis.

In an assembly of a covering shell for a prosthesis and a covering shell for a prosthetic foot, the covering shell can have a tubular shape and comprise at least one lug on a bottom edge of the tubular shape, the lug being capable of interlocking reversibly in the shell of the prosthetic foot, so as attach it removably to the tubular shape.

The assembly can comprise a ring with a first surface and a second surface, the first surface of the ring comprising the lug, the second surface of the ring being attached, preferably bonded, to the bottom edge of the tubular shape.

The shell or the assembly can comprise a gripping collet, said collet being capable of attaching an upper part of the tubular shape to a prosthesis socket so as to enable sliding between the tubular shape and the socket.

Advantageously, an assembly of a covering shell for an arm prosthesis and a covering shell for a hand prosthesis comprises the covering shell described above, the covering shell of the arm prosthesis being integral with the covering shell of the hand prosthesis or the covering shell of the hand prosthesis being removably attached to the covering shell of the arm prosthesis.

A method for manufacturing such a shell can advantageously comprise the following steps:

- obtaining a three-dimensional image of a limb,
- identifying in the image the parts of the limb having different hardnesses,
- defining on a digital model of the shell zones of different flexibility so as to correspond to the arrangement of said parts identified in said image,
- producing the shell from the digital model.

The manufacturing method can also provide that

- the three-dimensional image is obtained from a complete leg with its foot or from a complete arm with its hand or
- the shell comprises the shell of the leg prosthesis and the shell of the foot prosthesis or the shell of the arm prosthesis and the shell of the hand prosthesis.

Advantageously, the method also comprises the following steps:

- identifying in the image the shape of the leg,
- defining the digital model of the shell such that the shape of the shell corresponds to the shape of the limb as identified in the image.

The production step of the method described above is advantageously a step of 3D printing, preferably using powder melting, of the shell from said digital model.

The aim of the present invention is further that of providing a prosthesis of a given limb which reproduces the replaced limb more realistically.

The above aim is achieved by an exoskeletal structure of the prosthesis which resembles, to the touch, the replaced limb. The exoskeletal structure of the present invention resembles through the flexibility thereof the different parts felt when touching the replaced limb. Said exoskeletal structure is designed to provide a connection between a socket and a hand or foot prosthesis in order to form the prosthesis of the replaced limb.

In the preferred example, the exoskeletal structure of the prosthesis of a given limb comprises at least two zones of different flexibility, the arrangement of said zones in relation to one another corresponding to the arrangements of parts of the given limb having different hardnesses.

The exoskeletal structure preferably has a tubular shape. The exoskeletal structure of a prosthesis of a given limb is designed to provide a connection

- between a socket and a hand prosthesis or
- between a socket and a foot prosthesis in order to form the prosthesis of the limb.

The exoskeletal structure comprises at least two zones of different flexibility, the arrangement of said zones in relation to one another corresponds to the arrangement of the parts of the given limb having different hardnesses.

Said connection can be provided mostly by the first zone alone.

A first zone can differ from a second zone in relation to:

- a thickness and/or
- a material and/or
- a three-dimensional pattern in order to obtain a first zone having a different flexibility from a second zone.

The exoskeletal structure can have:

- a first zone having a lesser flexibility than a second zone, the first zone being arranged to coincide with a hard part of the limb, and/or
- a second zone having a greater flexibility than a first zone, the second zone being arranged to coincide with a soft part of the limb.

The exoskeletal structure can also have:

- a first zone and a second zone having different thicknesses, and
- the first zone and the second zone being obtained with a rib or with a recess.

The exoskeletal structure having a tubular shape can be designed so that:

- a flexibility of the exoskeletal structure remains mostly constant along a length of the tubular shape, and/or
- the flexibility of the exoskeletal structure mostly changes along a circumference of the tubular shape.

An exoskeletal structure of an arm prosthesis can have a zone having a greater thickness than a mean thickness of the exoskeletal structure, said zone being located on the exoskeletal structure like the radius or ulna is located under an arm's skin.

The exoskeletal structure of an arm prosthesis can also have a zone having a lesser thickness than a mean thickness of the exoskeletal structure, said zone being located on the exoskeletal structure like a muscle or a tendon is located under an arm's skin.

An outer surface of the exoskeletal structure can be mostly smooth and the changes in thickness can be located on an inner surface of the exoskeletal structure.

The exoskeletal structure can comprise in an interior of the structure at least one attachment device designed to attach an electronic component.

A material of the exoskeletal structure can comprise a thermoplastic polyurethane (TPU) and/or a material of the exoskeletal structure can comprise a polyamide.

A prosthesis of a given limb can comprise:

- an exoskeletal structure described above
- a socket and
- a foot prosthesis or a hand prosthesis,
- the exoskeletal structure being located:
- between the socket and the foot prosthesis or
- between the socket and the hand prosthesis in order to provide said connection.

In such a prosthesis, the exoskeletal structure can be integral with the socket to form a continuous material element and/or the exoskeletal structure can be integral with the foot or hand prosthesis to form a continuous material element.

A method for manufacturing an exoskeletal structure can comprise the following steps:

- obtaining a three-dimensional image of a limb,
- identifying in the image the parts of the limb having different hardnesses,
- defining on a digital model of the exoskeletal structure zones of different flexibility so as to correspond to the arrangement of said parts identified in said image,
- producing the exoskeletal structure from the digital model.

In the method, the three-dimensional image can be obtained from a complete leg with its foot or from a complete arm with its hand.

The method can comprise the following step:

identifying in the image the shape of the leg defining the digital model of the exoskeletal structure such that the shape of the exoskeletal structure corresponds to the shape of the limb as identified in the image.

The production step can comprise a step of 3D printing, preferably using powder melting, of the exoskeletal structure from said digital model.

BRIEF DESCRIPTION OF THE DRAWINGS

The present invention will be understood more clearly based on the following description of the appended drawings wherein.

DETAILED DESCRIPTION OF SPECIFIC EMBODIMENTS

An embodiment example of a covering shell for a prosthesis is illustrated in FIGS. 1, 3, 5, 6 and 8 to 10.

Figures 1, 2:
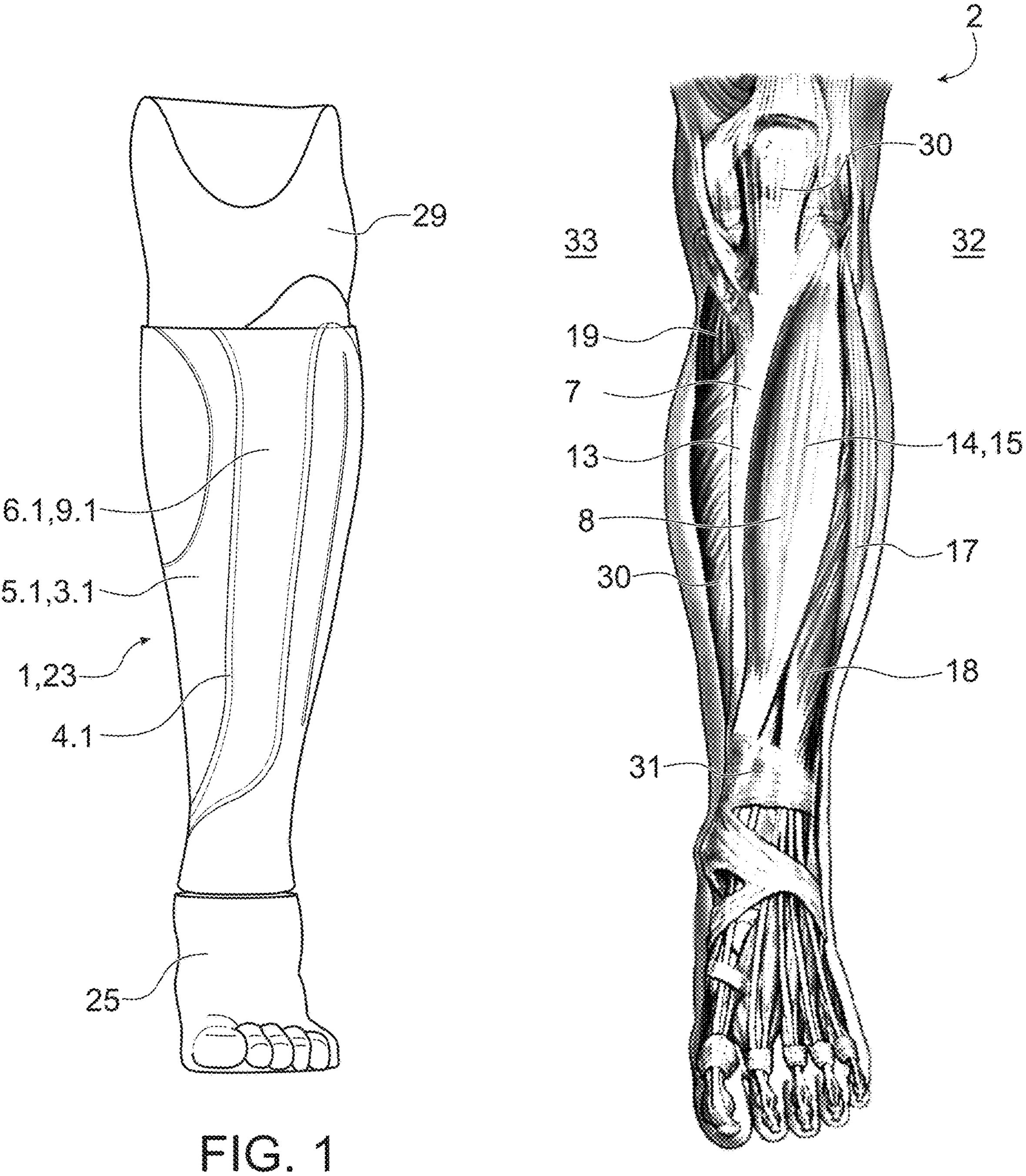
FIG. 1 shows an example of a covering shell for a prosthesis according to a first view.
FIG. 2 shows an anatomy of a given limb according to a first view.
Figures 3, 4:
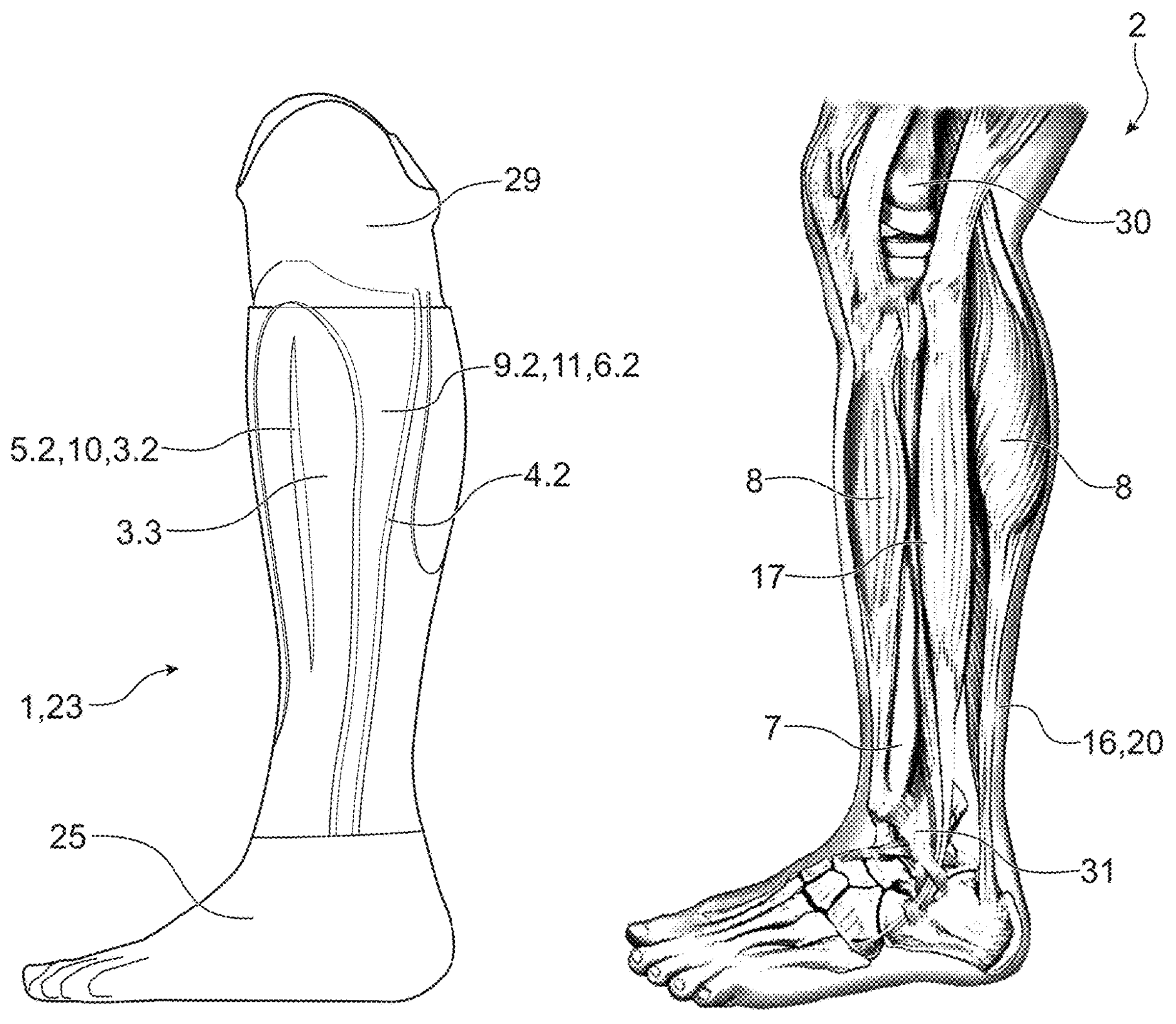
FIG. 3 shows an example of a covering shell for a prosthesis according to a second view.
FIG. 4 shows an anatomy of a given limb according to a second view.

FIGS. 2 and 4 show an anatomy of a given limb. The present example consists of the lower part of a leg. More specifically, it consists of a tibial part of a human leg.

Parts of the leg having different hardnesses (7, 8) are identified in said figures.

The tibia (13), which is one of the most important bones of this lower limb, spans between the knee (30) and the ankle (31). The tibialis anterior (14), which is one of the muscles (15) of the tibial part of the human leg, is also observed.

The tibia (13) is located under a skin (not shown) of the leg. This bone extends almost in a straight line between the knee and the ankle. The tibialis anterior (14) is located between the tibia and the skin. This muscle extends, under the skin, from an outer side (32) of the knee to an inner side (33) of the ankle and spans the tibia. It is thus possible to identify a part where the tibia located directly under the skin and a part where the tibialis anterior is located directly under the skin, between the skin and the tibia.

On touching the skin of the leg, it is thus possible to distinguish between a first hardness part (7) and a second hardness part (8), i.e. parts of the limb having different hardnesses.

To the touch, a part will feel soft if a muscle or a tendon is located directly under the skin. A part will feel hard if a bone is located directly under the skin.

In the present example, the part of the leg where the tibia is located directly under the skin is a part that feels hard, and the part of the leg where the tibialis anterior is located directly under the skin is a part that feels soft. Thus, two parts of the leg having different hardnesses are identified.

On touching more carefully, it is possible to differentiate even more than two parts of different hardnesses. For example, a part having more muscle tissue between the skin and the tibia will be harder than a part having less muscle tissue between the skin and the tibia. A part where a tendon is located will feel harder than a part where a muscle is located, but not as hard as a part where a bone is located.

Other soft and hard parts of the leg are formed by the position of the other bones, muscles and tendons on the leg, such as the fibularis longus (17), the extensor digitorum longus (18), the gastrocnemius (19) or Achille's tendon (20). A plurality of parts of the leg having different hardnesses are thus identified.

Parts of a limb having different hardnesses have been exemplified for a lower leg, but they can also be found on the upper part of the leg, on the arm and at other areas of the body.

The arrangement of the parts of the limb having different hardnesses, i.e., the demarcation of a hard or soft zone and the relative position of a hard zone relative to a soft zone are dependent on the anatomy of the chosen limb. This arrangement is a characteristic of the given limb which is replaced by the prosthesis.

The present embodiment example relates to a shell for a leg prosthesis, but the invention is also applicable to other parts of the body having different hardnesses.

Figures 5, 6:
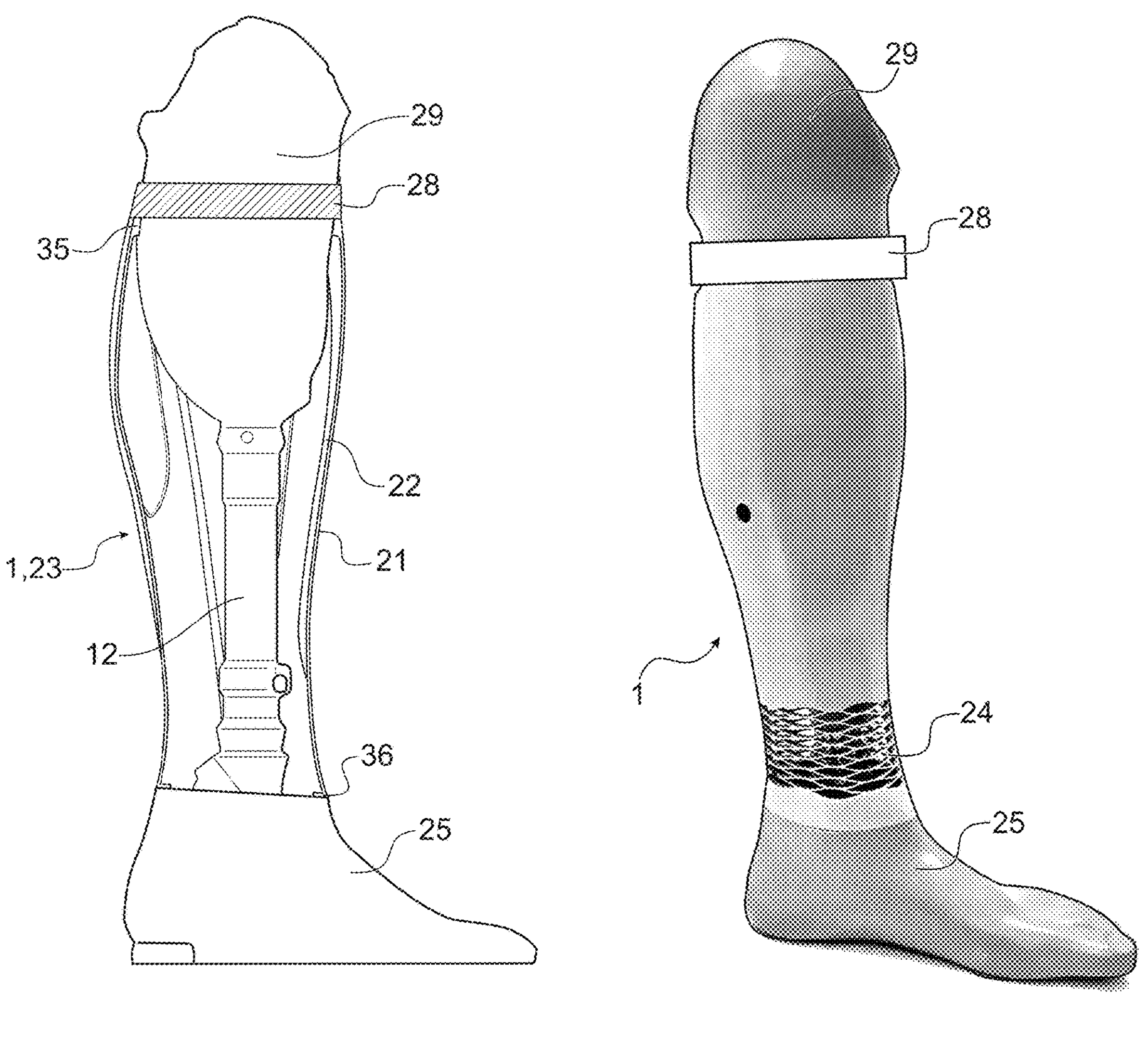
FIG. 5 shows a longitudinal sectional view of a covering shell for a prosthesis and a prosthesis.
FIG. 6 shows a perspective view of another example of a covering shell for a prosthesis and a prosthetic foot shell.

FIGS. 1, 3 and 5 show a covering shell (1) for a leg prosthesis (12). In FIGS. 1, 3 and 5, a covering shell having a tubular shape (23) and a shell for a prosthetic foot (25) are identified. The prosthesis is attached via a prosthesis socket (29) to a user's stump (FIG. 5).

FIG. 5 shows an inner surface (22) and an outer surface (21) of the shell. The thickness of the shell is a quantity of material between said inner surface and outer surface of the shell. In FIGS. 1 and 3, a first thickness (3.1, 3.2, 3.3) of the shell, a second thickness (9.1, 9.2) and a change of thickness (4.1, 4.2) located between the first (3.1, 3.2, 3.3) and the second (9.1, 9.2) thickness are also identified.

Tubular shape refers to a cylindrical shape that cross-sections having a variable shape and size can have. The tubular shape can also be curved and thus mostly follow a non-straight axis. The shell shown in FIG. 5 thus has a cross-section of shape and size which is different at a calf level and at an ankle level. This tubular-shaped shell could also be curved and thus follow a socket (29) which has an angle in relation to the prosthesis (12). A shell which has a leg or arm shape thus has a tubular shape.

The change of thickness thus demarcates a first zone (5.1, 5.2) having the first thickness (3.1, 3.2, 3.3) from a second zone (6.1, 6.2) having the second thickness (9.1, 9.2).

The shell has a flexibility dependent on the thickness thereof. Thus, if the first zone (5.1, 5.2) has a greater thickness than the second zone (6.1, 6.2), the first zone (5.1, 5.2) will have a lesser flexibility than the second zone (6.1, 6.2).

In other words, if the first zone (5.1, 5.2) has a greater thickness than a mean thickness of the shell and if the second zone (6.1, 6.2) has a lesser thickness than a mean thickness of the shell, the first zone (5.1, 5.2) will have a lesser flexibility than the second zone (6.1, 6.2).

Zones of different flexibility can also be obtained with a difference in material. A first zone can be made of a first material, a second zone can be made of a second material. The first material can be less flexible than the second material. Two zones of different flexibilities are thus obtained.

A difference in material can be understood as a difference in chemical composition of the material. Thus, a polymer used can be more flexible if it comprises an added chemical component, for example if it comprises a plasticizer.

A difference in material can be understood as a difference in macroscopic composition. Thus, a second zone can comprise a thermoplastic polyurethane. A first zone can comprise thermoplastic polyurethane and also carbon fibers. Two zones of different flexibility are thus obtained, the first zone having a lesser flexibility than the second zone due to the properties of the carbon fibers.

It is also possible to obtain zones of different flexibility with a difference in three-dimensional pattern impregnated on the zone. For example, a second zone can comprise a thermoplastic polyurethane. A first zone can comprise thermoplastic urethane impregnated with a three-dimensional deformation rendering said zone less flexible.

On touching the shell, the zone of a greater flexibility gives the impression of touching a soft part of a limb whereas the zone of lesser flexibility gives the impression of touching a hard part of a limb.

The covering shell can also comprise a plurality of zones having different flexibilities. Two, three, four or more zones can be provided, the set of zones having two, three or more different flexibilities. For example, five zones can be provided, the set of five zones having three different flexibilities.

In this way, it is possible to obtain a plurality of different flexibilities. A covering shell can thus be obtained in which, to the touch, a plurality of different hardnesses are felt. In this way, the covering shell can even more specifically resemble touching an anatomy of a limb because, when touched more carefully, it is possible to differentiate more than two parts of different hardnesses on the anatomy of a limb. It is also possible to vary a combination of a thickness, a material and/or a three-dimensional structure to obtain zones of different flexibility.

Different thicknesses of the shell can be made by varying a thickness of a material used for manufacturing the shell. It is also possible to use a material comprising several layers and to vary from one position to another the number of layers to arrive at the different thickness of the shell. It is also possible to use layers made of different materials.

On comparing the shell in FIG. 1 with the anatomy of FIG. 2, it is observed that the arrangement of the zones of different flexibility (5.1, 5.2, 6.1, 6.2) in relation to one another corresponds to the arrangement of the parts of the limb having different hardnesses (13, 14, 17).

It is observed in FIG. 1 that the second zone (6.1) is arranged mostly longitudinally curving downwards. The first zone (5.1) is arranged so as to widen from a top to a bottom.

The first zone (5.1) is thus arranged in relation to the second zone (6.1) on the shell like the tibia (13) is arranged in relation to the tibialis anterior (14).

The arrangement of the zones varies from one patient to another, as the position of the bones, muscles and tendons varies from one patient to another.

In the present example, the first zone (5.1) has a greater thickness than the second zone (6.1). Said first zone thus gives to the touch the impression of being harder than the second zone. The second zone gives the impression of being softer than the first zone.

On touching the shell, the user thus receives a similar sensation to touching a lower part of a human leg. The first zone (5.1) will feel like touching the tibia and the second zone like touching the tibialis anterior muscle. On sliding a finger between the first zone (5.1) and the second zone (6.1), the change of flexibility, induced by the change of thickness of the shell, is perceived as a change of firmness, between a soft part and a hard part of a human leg.

Similarly, it is observed in FIGS. 3 and 4 that a second zone (6.2) having a lesser thickness is arranged on the shell like the fibularis longus (17) on the tibial part of a leg.

A change of thickness to demarcate zones of different flexibility can also be obtained with a rib or with a recess on the covering shell.

FIG. 3 shows a rib (10) on the covering shell to obtain a lesser flexibility at the position where the rib is located. FIG. 3 also shows a recess (11) to obtain an increased flexibility at the position where the recess is located.

A rib or a recess has a change of thickness of the shell. A shell having a rib comprises a first zone and a second zone having different thicknesses. For example, the zone of the rib itself can be identified as the first zone of greater thickness. The second zone of lesser thickness in relation to the first zone is, in this case, the zone which is located outside the area of the rib.

A use of ribs and recesses enables a particularly fine arrangement of zones of different flexibility.

Advantageously, the shell comprises a thermoplastic polyurethane (TPU) and/or a polyamide.

The thermoplastic polyurethane has advantages for manufacturing a shell for a prosthesis. It enables a good emulation of a contralateral limb, this material can be placed in water and can be washed easily. Under the effect of a shock, the shell comprising this material is deformed and makes no noise. Due to the elasticity and flexibility properties thereof, TPU is particularly suitable for the manufacture of zones of different flexibility to emulate a physiological touch. A shell comprising this material is light and does not add excessive weight to the prosthesis.

The shell can be manufactured using a 3D printing method, for example by powder melting.

The first zone (5.1, 5.2) and the second zone (6.1, 6.2) can have a longitudinal shape (FIG. 1, 2) on the covering shell, the longitudinal shape extending along an extension of the limb.

In the embodiment example shown in FIGS. 1, 3, and 5, the covering shell has a tubular shape. The first thickness (3.1, 3.2, 3.3) and the second thickness (9.1, 9.2) remain mostly constant along a length of the shell. The thickness shows a change mostly along a circumference of the tubular shape of the shell.

In the specific case of ribs or recesses, said ribs and recesses extend mostly along a length of the tubular shape.

An arrangement as described above corresponds particularly well for the manufacture of a shell for a prosthesis for an arm or for a leg.

The muscles, tendons and bones of the arm and the leg extend mostly along a length of the arm or the leg. For this reason, on touching an arm or a leg, minor changes in hardness are felt along the limb. A rib or a recess provided along a length of the tubular shape induces a change in hardness felt if a user moves their finger along the circumference of the shell, the hardness remaining constant along the length of the tubular shape. To the touch, the shell thus reproduces a similar behavior to a leg or an arm.

FIG. 5 shows the covering shell (1) for a tibia prosthesis and a shell for a prosthetic foot (25). A lower limb prosthesis (12), more specifically a tibia prosthesis, comprising a prosthesis socket (29) is also shown. In the example shown, the connection between the socket and the foot prosthesis is provided by an internal element (12), for example a rod or a bar.

Similarly (image not shown), a rigid cage can be provided to provide a connection between the socket and the foot prosthesis. In this case, the cage replaces the tube mentioned above. The cage provides the stability and transmission of a force between the foot prosthesis and the socket. In this case, the covering shell houses the cage therein and thus covers the cage.

The use of a cage is particularly suitable for the use of an arm prosthesis. The cage provides the connection between the socket and a hand prosthesis. The prosthesis itself is presented in the form of a cage made of rigid material, said cage being attached by one end to a prosthesis socket. The hand prosthesis is attached to the other end of the cage. The covering shell is attached to the cage. A prosthetic hand shell can be attached to the prosthetic hand. The cage can be manufactured from carbon fiber or from thermoplastic polyamide, for example from PA12. The covering shell for the arm prosthesis and the covering shell for the arm prosthesis can be manufactured in two parts. They can also be manufactured integral with one another and, in this way, cover in a single continuous material element the arm prosthesis and the hand prosthesis.

The shell has a tubular shape (3) comprising an inner surface (22) and an outer surface (21). The covering shell houses the prosthesis therein and thus covers the prosthesis. The covering shell is fitted with the bottom edge (36) thereof on the shell for a prosthetic foot (25).

Advantageously, the outer surface (21) of the shell is mostly smooth in relation to the changes (4.1, 4.2) demarcating the zones of different flexibility.

The expansion or contraction of the material which forms a greater thickness (for example a rib) or lesser thickness (for example a recess) takes place towards an interior of the shell (FIG. 5), in the direction of the prosthesis. The surface remains, in this way, smooth.

More specifically, the inner surface (22) moves away from or closer to the outer surface (21) to induce a change of the thickness. The whole of the outer surface and the inner surface, forming a wall of the shell, can mold a shape resembling an anatomy of a limb. It is observed, for example in FIG. 5, that the wall between the outer surface (21) and the inner surface (22) curves from a top to a bottom to make the shell resemble, at this position, a calf. A smooth outer surface means that the inner surface, while following the shape of the outer surface, moves away from and closer to the outer surface to form zones of different thickness. In the specific case of ribs (10) and/or recesses (11), mostly smooth means that the rib and/or the recess is located inside the shell.

The shell imparts by the smooth exterior thereof furthermore a physiological touch, corresponding to smooth skin having different hardnesses to the touch.

It is also possible to provide a mostly smooth inner surface and to locate changes (4.1, 4.2) on an outer surface. Thus, the ribs and/or the recesses can be oriented towards an outer surface.

In addition, the changes (4.1, 4.2) can be located on the outer surface and on the inner surface.

FIG. 6 shows the covering shell (1) for a leg prosthesis, the shell having a tubular shape and comprising a joint zone (24). The shell for a prosthetic foot (25), which can be manufactured from polyurethane foam, is also found.

The covering shell (1) is fitted on the shell for a prosthetic foot. Inside the covering shell, the prosthesis (12) also shown in FIG. 5 is positioned.

In the example shown, the joint zone (24) is provided at an ankle, but it could also be located at a knee if the shell is provided for another type of prosthesis, such as a prosthesis for a whole leg.

In the present example, the joint zone (24) includes openings in the covering shell. More specifically, in the present example, these are openings having a rhombus shape, located at the ankle. Other opening shapes can be used, for example in the shape of a circle or rectangle. Due to the material lacking in the openings, the shell is more flexible at the location of the openings than elsewhere. The shell can thus be formed readily at the ankle to follow the movement of a prosthesis when walking.

The rhombus-shaped openings also make it possible to access the prosthesis located inside the covering shell. In this example (FIG. 6), it is possible to access the prosthesis through rhombus-shaped openings. The foot of the prosthesis can thus be disconnected from the other parts of the prosthesis without having to modify the shell of the prosthesis. Also, maintenance procedures are possible without needing to remove the covering shell. Other openings, for example at the calf, above the joint zone (24) (see FIG. 6), can be provided to enable access to other elements for setting the prosthesis (for example a valve, an oriented slot). The distribution of these openings is specific to each prosthesis and dependent on each patient's needs.

FIGS. 7 to 10 show the covering shell (1) having the joint zone (24) and the shell for a prosthetic foot (25). The shell for a foot has hollows (34) on an open side.

Figure 8:
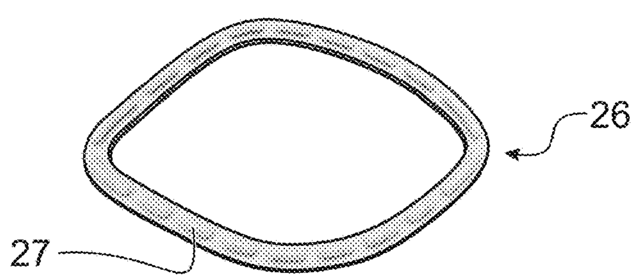
FIG. 8 shows a detailed view of the covering shell for a prosthesis in FIG. 6 comprising lugs at a connection end to the prosthetic foot shell.
Figure 8:
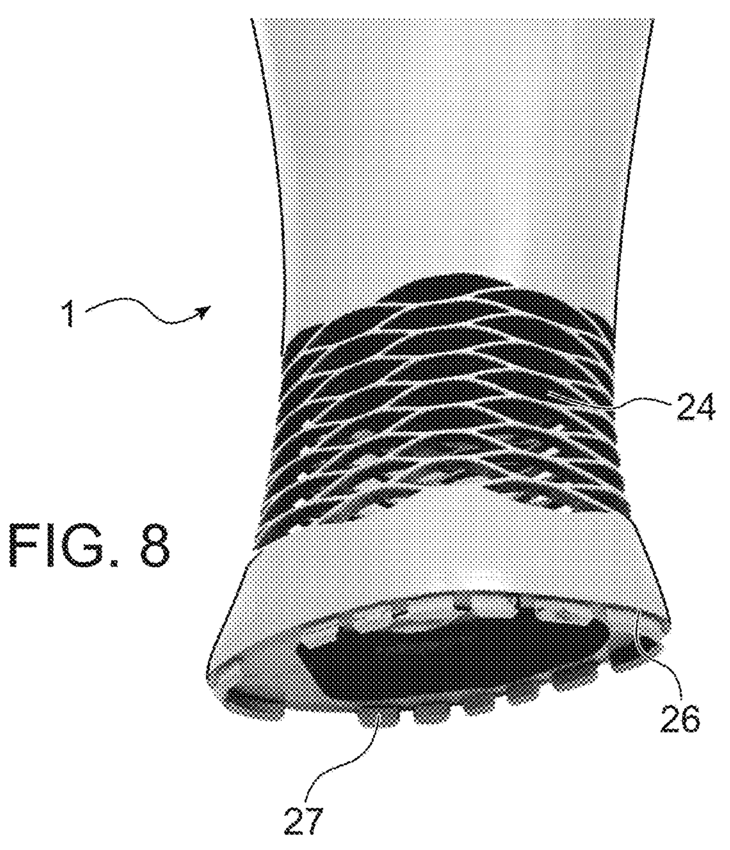

FIG. 8 also shows lugs (27) on a bottom edge of the shell (36), but in some cases a single lug could suffice to provide a stable connection.

According to a first embodiment, the lug (27) and the covering shell (1) are formed of one piece. The lugs are integral with the covering shell.

Figure 7:
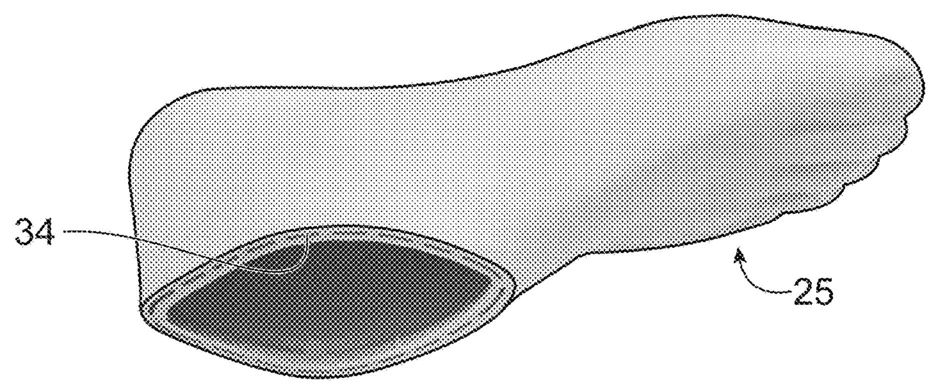
FIG. 7 shows an example of a shell for a prosthetic foot and a ring comprising lugs.

FIG. 7 shows a ring (26) having a first surface and a second surface. The second surface is equipped with lugs (27). According to a second embodiment, the first surface of the ring (26) is attached, preferably bonded, to the bottom edge of the prosthesis shell.

The covering shell thus comprises at least one lug (27) on a bottom edge (36).

Figure 9:
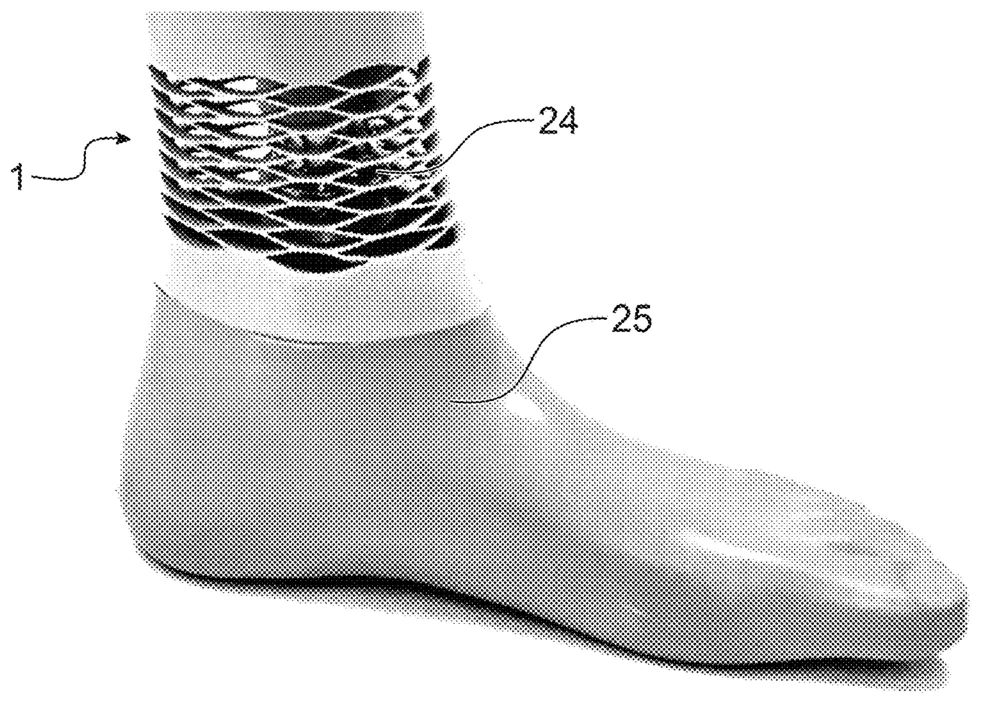
FIG. 9 shows an enlarged view of a covering shell fitted on the prosthetic foot shell.

This bottom edge will be facing the shell for a prosthetic foot (FIG. 9, 10).

Figure 10:
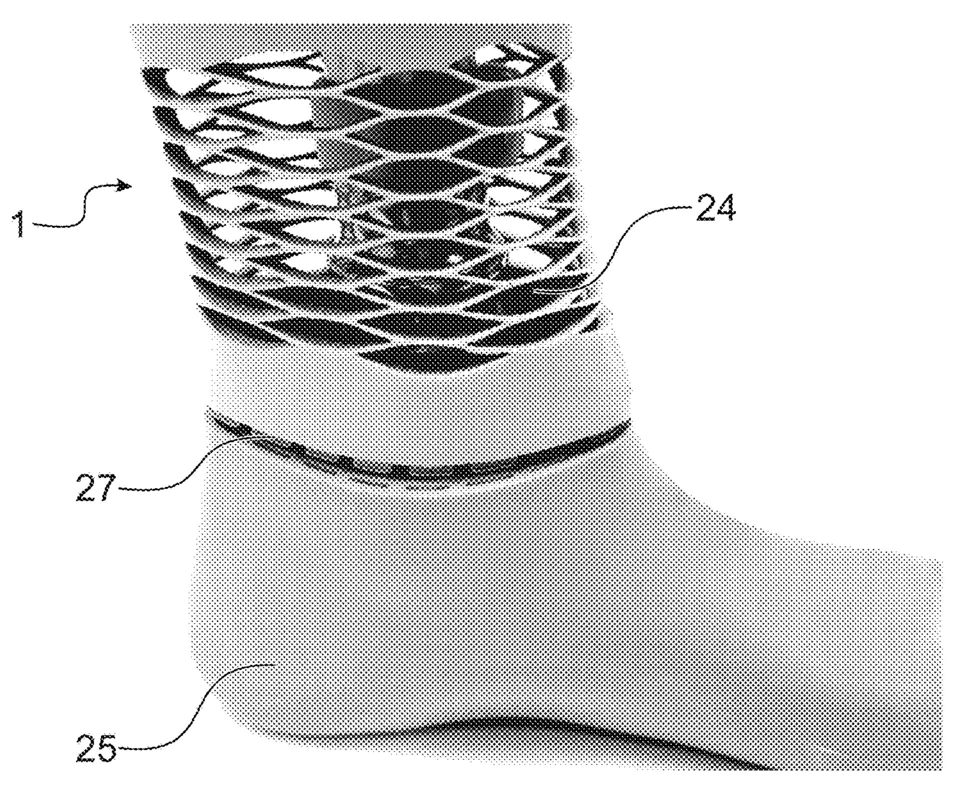
FIG. 10 shows the covering shell in FIG. 9 separated from the shell for a prosthetic foot.

The lugs (27) are in this way outwardly oriented, in the direction of the shell for a foot (FIG. 10). The covering shell (1) can be attached to the shell for a foot (25) to form a complete covering for a prosthesis. On assembly, the lugs of the rings interlock reversibly in the holes (34) provided on the open side of the shell for a prosthetic foot (FIG. 9, 10). The assembly being reversible, the covering shell can be separated from the shell for a foot by gently pulling one of these two parts. The tibial prosthesis is thus disassembled easily without needing to modify, such as by cutting or deforming, the covering shell.

The prosthesis located inside the covering shell is accessed, if necessary with a tool, through the openings of the joint zone. Other openings can be present to access different setting elements of the prosthesis, such as a valve or an oriented slot.

It is thus possible to disassemble the prosthetic foot from the remainder of the prosthesis. Then, the prosthetic foot is removed from the remainder of the prosthesis by separating the covering shell from the shell for a prosthetic foot by uncoupling the lugs from the holes (34).

According to another embodiment, the covering shell can be integral with the shell of the prosthetic foot. According to this embodiment, the shell forms a continuous material element with the prosthetic foot.

FIGS. 5 and 6 also show a gripping collet (28) on an upper part (35) of the covering shell.

The gripping collet attaches the shell (1) to the prosthesis socket (29). The collet is arranged so as to enable slight sliding between the shell and the socket so as that the aesthetic is not constrained when walking with the prosthesis comprising the shell.

The shell described above can be manufactured advantageously with the method described hereinafter.

In a first step, a three-dimensional image of a limb is obtained.

For example, a patient's non-amputated limb is digitized using a 3D scanner to obtain said image. Via said image, a representation of the surface of this limb is obtained, i.e. a three-dimensional digital representation of the limb is obtained. The digital representation of the limb is a three-dimensional surface.

Alternatively, a three-dimensional image obtained from a data library could be used. In this case, said image is obtained from a library of morphotypes based on the patient's height and weight.

A scanned image of the patient's limb obtained before the limb was amputated could also be used.

In the present example, a digital representation of a tibial part of a leg, i.e., a digital representation of a lower part of the leg as shown in FIGS. 2 and 4, is obtained.

Similarly, a digital representation of a foot can also be obtained. As described above, it is possible to use a 3D scanner or to retrieve an image from an image library.

Similarly, a digital representation of a leg with its foot can be obtained, using a 3D scanner or by retrieving an image from an image library.

Similarly, a digital representation of a hand, an arm with its hand, or an arm and a hand separately can also be obtained.

In a second step, the parts of the limb having different hardnesses (7, 8) are identified on the digital representation of the limb. This identification can be made automatically, manually by an operator or by an operator assisted by an algorithm. This identification can be made on the complete digital representation or only on a part of the digital representation. In the example of a digital representation of a leg with its foot, this identification can be made, for example, only on the part of the leg excluding the foot. Following this step, a demarcation of the parts having different hardnesses can be plotted on the representation of the limb. In other words, an arrangement of the parts of different hardness in relation to one another can be plotted on the representation of the limb.

For example, on a digital representation of a tibial part of a leg, the part corresponding to the tibia and the part corresponding to the tibialis anterior are identified. Then, on the digital representation, a line is plotted to demarcate an extension of the tibia and the tibialis anterior under the skin.

In a third step, the aesthetic is designed. The second and the third step can be carried out using computer-aided design (CAD) software.

On a digital model of the shell, a zone is defined by defining the shape thereof. A zone shape is then plotted on the surface of the shell. Then, a flexibility of this zone is defined. For example, the thickness that the material of the shell will have in this zone is set. At the end of this step, an arrangement of zones of different flexibilities, for example obtained with different thicknesses, is defined on the shell.

The shape and flexibility of the zones are defined so as to correspond to the arrangement of the parts of the limb having different hardnesses.

In an example using different thicknesses, on the shell, a first zone having a greater thickness will be located in relation to a second zone having a lesser thickness as a harder part of the limb is located in relation to a softer part on the digital representation of the limb, said parts being identified previously as described above.

To verify the arrangement of said zones in relation to one another and the correspondence to the arrangement of the parts of the limb, the digital representation of the shell for a prosthesis can be projected on the digital representation of the limb.

In this way, a zone having a greater thickness than a mean thickness is arranged to coincide with a hard part of the limb and/or a zone having a lesser thickness than a mean thickness is arranged to coincide with a soft part of the limb.

For example, on a digital model of the shell as seen in FIG. 1, a first zone (5.1) corresponding by the shape thereof to the tibia part (13) is plotted. The tibia part has been previously identified on the digital representation of the leg.

Then, a second zone (6.1) is plotted on the digital model of the shell corresponding by the shape thereof to the tibialis anterior part (14), as previously identified on the digital representation of the leg.

Then, a greater thickness is associated with the first zone and a lesser thickness with the second zone.

The shell manufactured will thus be less flexible at the first zone than at the second zone, like a leg is harder at a part corresponding to the tibia and softer at a part corresponding to the tibialis anterior. The shell imparts in this way a physiological touch for a user.

It is also possible to give the shell the shape of the limb as deduced from the digital representation of the original limb. The shell adopts, in this way, the shape of the limb. The shell can thus adopt the three-dimensional shape of the leg, for example of the tibial part, the arm, the foot, or the hand. The shell can also adopt the shape of the leg with its foot or of the arm with its hand and thus reproduce a complete shape of a limb.

A shell which adopts the shape of the limb and imparts at the same time a physiological touch is particularly suitable for giving a user a natural feeling when wearing their prosthesis.

The manufacturing method can also comprise a step of 3D digitization of the prosthesis (12) to be covered by the shell, to adapt the shell to the prosthesis during the computer-aided design process.

The shell can then be manufactured using a 3D printing method from the digital model. More specifically, powder melt 3D printing can be used, for example with TPU.

It is thus possible to manufacture a covering for a leg prosthesis or for an arm prosthesis.

In the case of a leg prosthesis, the covering shell can be manufactured using a digital representation of a complete leg with its foot, with the method described above. In this case, it is possible to manufacture a complete covering for the foot prosthesis and for the leg prosthesis. The covering for the leg prosthesis and the covering for the foot prosthesis can be manufactured in two separate parts. The covering for the leg prosthesis and the covering for the foot prosthesis can also be manufactured integral with one another. In the latter case, a covering for a prosthesis is obtained, which can cover in a single continuous material element the foot prosthesis and the leg prosthesis. In other words, using a digital representation of a complete leg with its foot, a shell covering the leg prosthesis and the foot prosthesis can be manufactured with a single continuous material element. It is possible to impart on this covering the shape as defined by the digital representation. In other words, the covering of the leg prosthesis reproduces the shape of the leg according to the digital representation and the covering of the foot prosthesis reproduces the shape of the foot according to the digital representation. In summary, a covering for a complete prosthesis, including a tibial prosthesis with a foot prosthesis, can be obtained using a representation of a complete leg with its foot. This covering can have the shape of the complete leg with its foot, and impart, in places or completely, a physiological touch.

Similarly, a covering for an upper limb prosthesis, for example of an arm, can be obtained. In the case of an arm prosthesis, the covering can also be manufactured using a digital representation of a complete arm with its hand, with the method described above. The covering for the arm prosthesis and the covering for the hand prosthesis can be manufactured in two separate parts or integral with one another. In other words, it is possible to manufacture using a digital representation of the complete arm with its hand a shell covering the arm prosthesis and the hand prosthesis with a single continuous material element. The covering can adopt the shape as defined by the digital representation of the arm with or without its hand.

An embodiment example of an exoskeletal structure of a prosthesis is illustrated in FIGS. 11, 13, 15, 16 and 18 to 20.

Figures 11, 12:
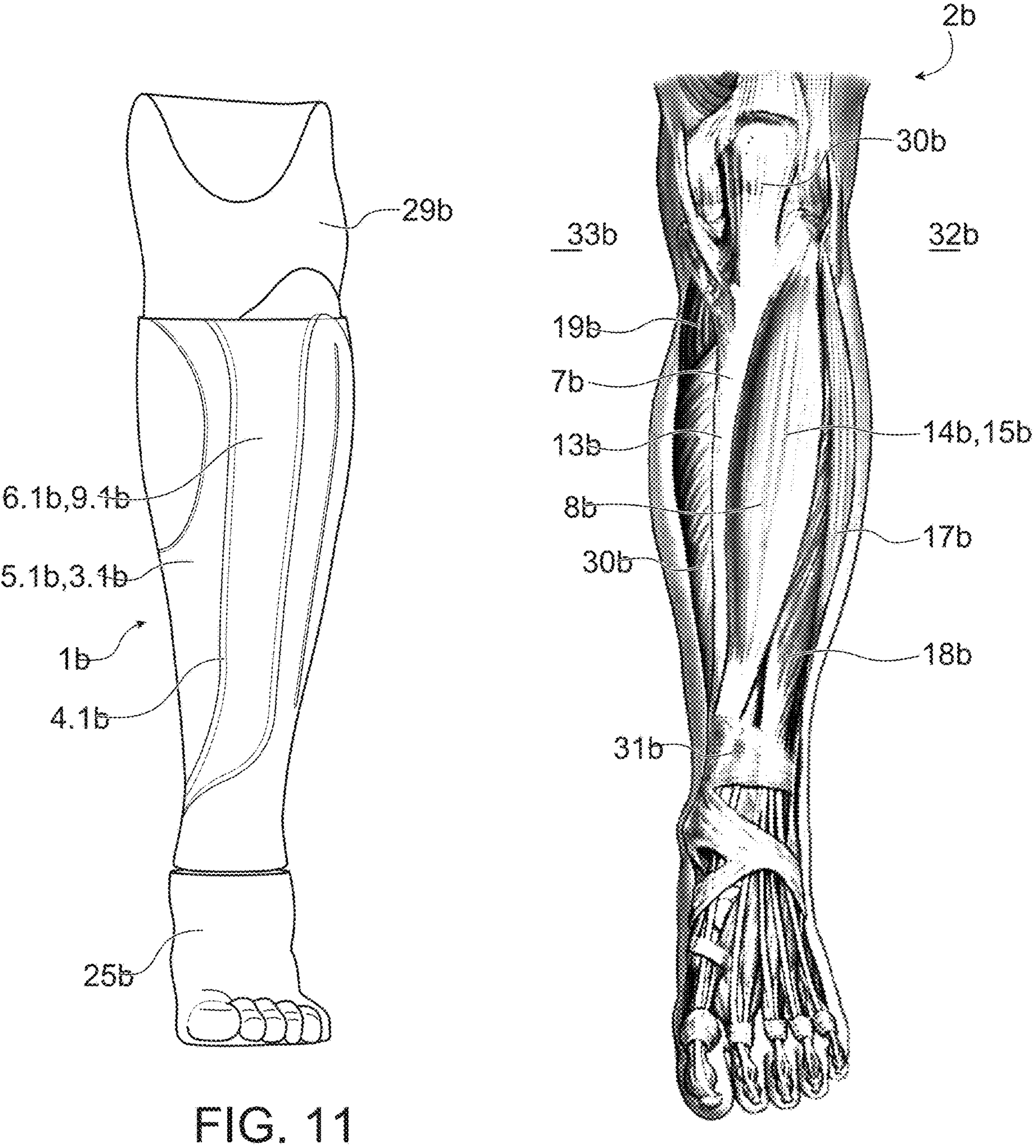
FIG. 11 shows a first example of a prosthesis comprising an exoskeletal structure according to a first view.
FIG. 12 shows an anatomy of a given limb according to a first view.
Figures 13, 14:
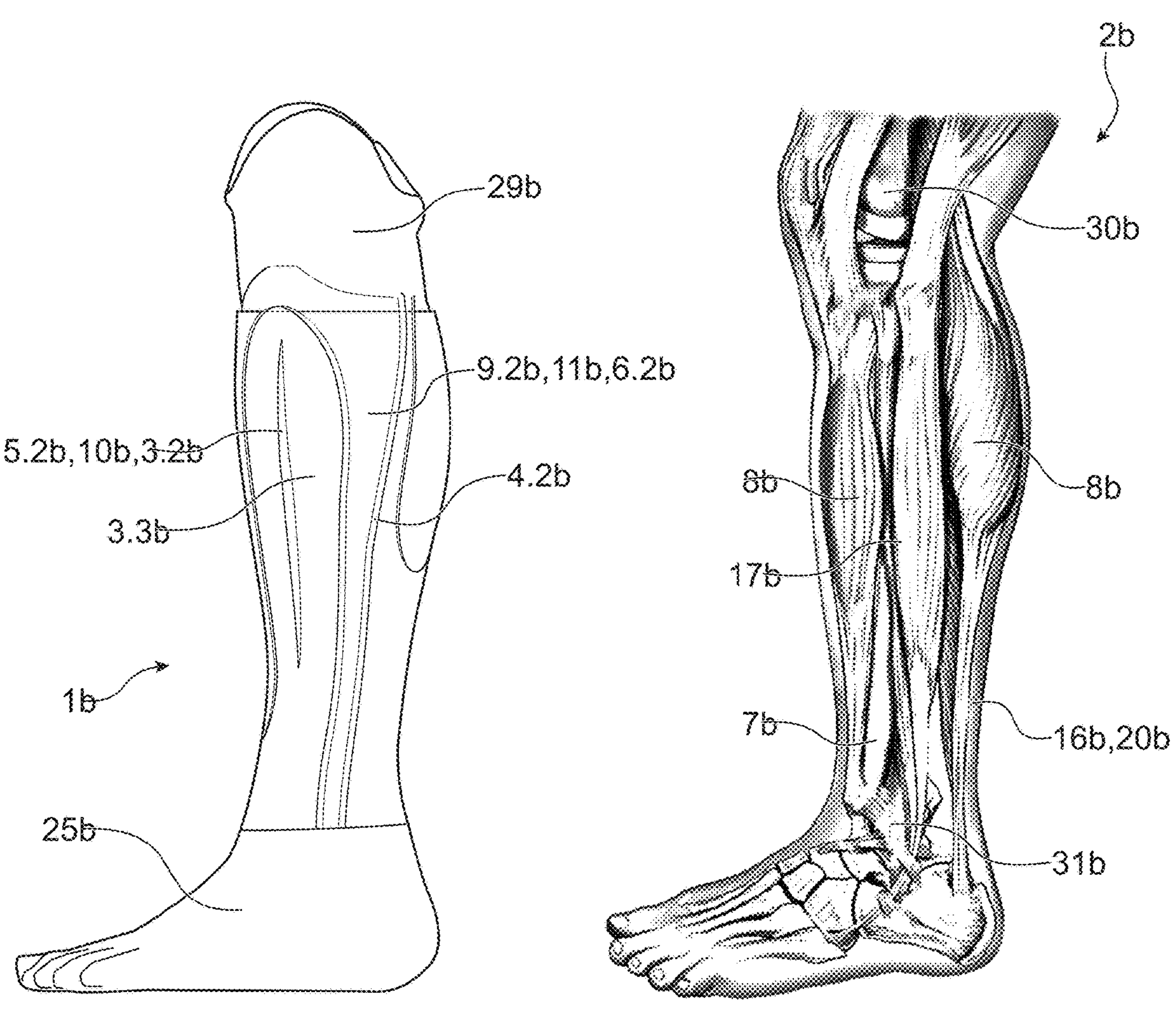
FIG. 13 shows a first example of a prosthesis comprising an exoskeletal structure according to a second view.
FIG. 14 shows an anatomy of a given limb according to a second view.
Figure 17:
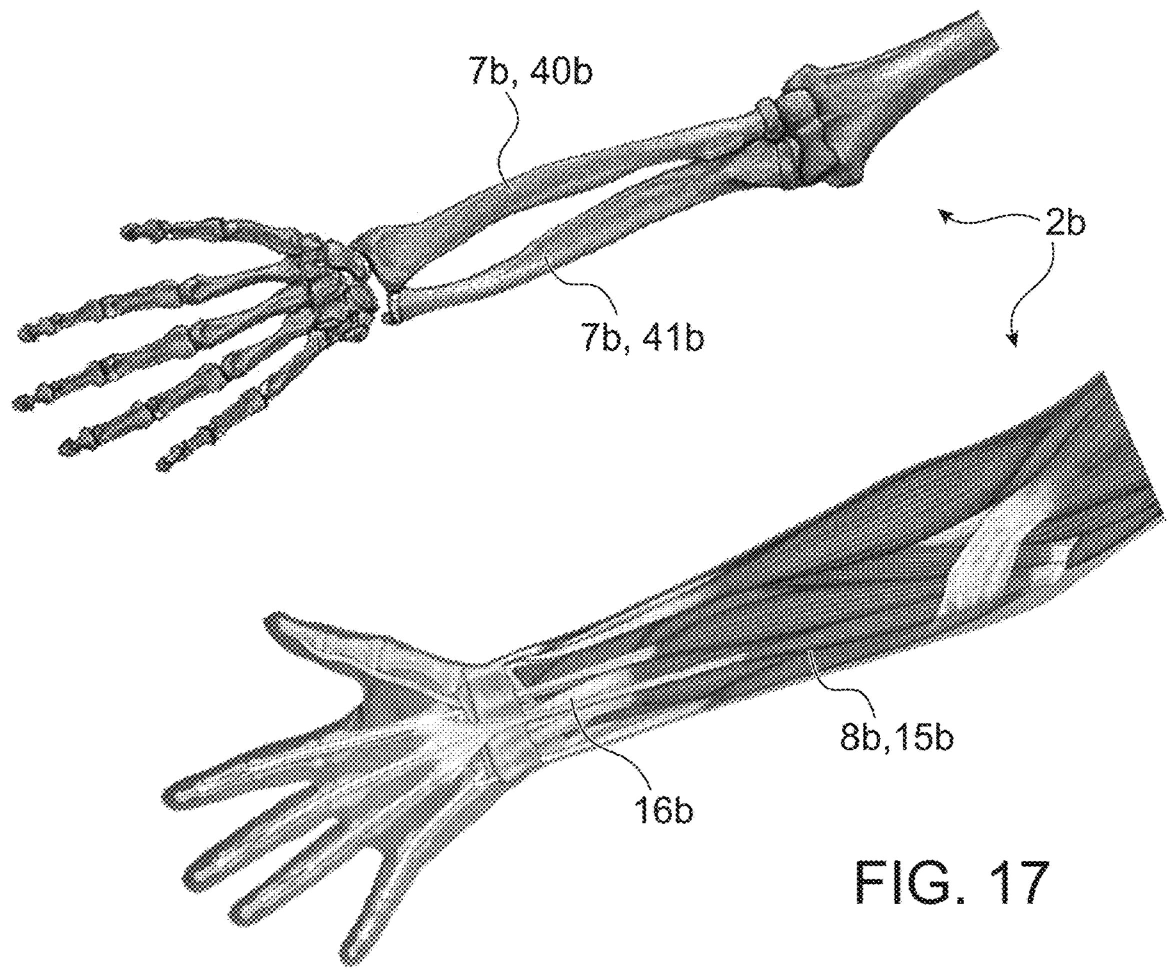
FIG. 17 shows an anatomy of another given limb.

FIGS. 12, 14 and 17 show an anatomy of a given limb. The present example consists of the lower (tibial) part of a leg or a forearm.

Parts of the leg or arm having different hardnesses (7*b*, 8*b*) are identified in said figures.

The tibia (13*b*), which is one of the most important bones of this lower limb, spans between the knee (30*b*) and the ankle (31*b*). The tibialis anterior (14*b*), which is one of the muscles (15*b*) of the tibial part of the human leg, is also observed. In an arm, the radius and ulna span between the wrist and the elbow and thus provide a connection between the hand and the upper arm. The flexor, which a prominent muscle of the arm, is also observed.

The tibia (13*b*) is located under a skin (not shown) of the leg. This bone extends almost in a straight line between the knee and the ankle. The tibialis anterior (14*b*) is located between the tibia and the skin. This muscle extends, under the skin, from an outer side (32*b*) of the knee to an inner side (33*b*) of the ankle and spans the tibia. It is thus possible to identify a part where the tibia located directly under the skin and a part where the tibialis anterior is located directly under the skin, between the skin and the tibia.

On touching the skin of the leg, it is thus possible to distinguish between a first hardness part (7*b*) and a second hardness part (8*b*), i.e., parts of the limb having different hardnesses. Similarly, on an arm, parts of different hardnesses corresponding for example to the ulna (bone) and the flexor (muscle) are identified.

To the touch, a part will feel soft if a muscle or a tendon is located directly under the skin. A part will feel hard if a bone is located directly under the skin.

In the present example, the part of the leg or arm where the tibia or ulna is located directly under the skin is a part that feels hard, and the part of the leg or arm where the tibialis anterior or flexor is located directly under the skin is a part that feels soft. Thus, two parts having different hardnesses are identified.

On touching more carefully, it is possible to differentiate even more than two parts of different hardnesses. For example, a part having more muscle tissue between the skin and the tibia will be harder than a part having less muscle tissue between the skin and the tibia. A part where a tendon is located will feel harder than a part where a muscle is located, but not as hard as a part where a bone is located.

Other soft and hard parts of the leg are formed by the position of the other bones, muscles and tendons on the leg, such as the fibularis longus (17*b*), the extensor digitorum longus (18*b*), the gastrocnemius (19*b*) or Achille's tendon (20*b*). A plurality of parts of the leg having different hardnesses are thus identified.

Parts of a limb having different hardnesses have been exemplified for a lower leg, but they can also be found on the upper part of the leg, on the arm and at other areas of the body.

The arrangement of the parts of the limb having different hardnesses, i.e., the demarcation of a hard or soft zone and the relative position of a hard zone relative to a soft zone is dependent on the anatomy of the chosen limb. This arrangement is a characteristic of the given limb which is replaced by the prosthesis.

The present embodiment example relates to an exoskeletal structure of a prosthesis of a limb and more specifically an exoskeletal structure of a prosthesis of an arm or a leg. The invention is applicable, however, in the same way to other parts of the body having different hardnesses.

Figure 15:
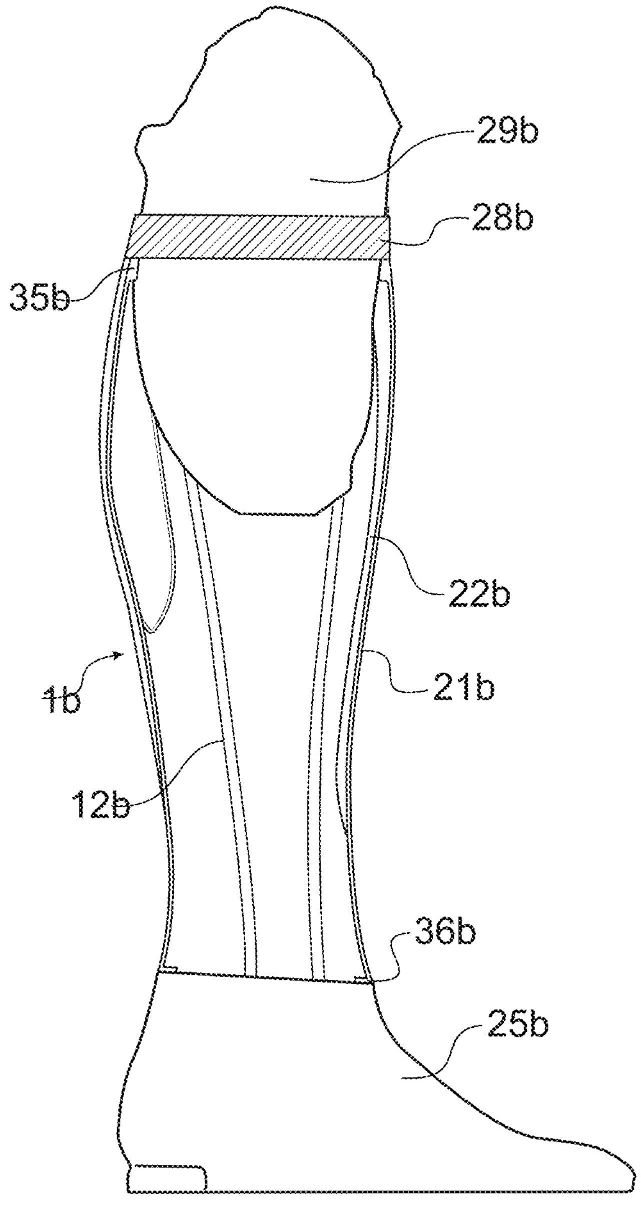
FIG. 15 shows a longitudinal sectional view of a prosthesis according to the first example comprising an exoskeletal structure.

FIGS. 11, 13 and 15 show a leg prosthesis (12*b*). FIGS. 16, 18, 19, 20 and 21 show an arm prosthesis.

In FIGS. 11, 13, 15, 16, and 19, a socket (29*b*) is identified. The socket (29*b*) is adapted to be attached to an arm stump for an arm prosthesis or to a leg stump for a leg prosthesis. The socket thus attaches the prosthesis to the body. A foot prosthesis (25*b*) and a hand prosthesis (37*b*) are also identified. The foot prosthesis and the hand prosthesis help a patient perform the tasks performed by a foot or a hand of a natural limb. More specifically, the foot prosthesis can support the weight of the body and provide movement during walking. The hand prosthesis can, for example, lift a weight, or push an object. In both cases, a force can be transmitted between the foot prosthesis or the hand prosthesis and the socket to provide movement. In this same way, a force must be transmitted if a user settles on the foot prosthesis or the hand prosthesis.

An exoskeletal structure of the prosthesis (1*b*) is also identified. The exoskeletal structure provides a connection between the socket (29*b*) and the foot prosthesis (25*b*) or the hand prosthesis (25*b*). The exoskeletal structure is placed between the socket and the foot prosthesis or the hand prosthesis. The socket can be attached on one side of the exoskeletal structure. The foot or hand prosthesis can be attached on the other side of the connection.

The exoskeletal structure provides the connection between the socket and the foot or hand prosthesis by enabling the transmission of force to move the foot or hand prosthesis. Similarly, the exoskeletal structure transmits force between the socket and the prosthetic foot or prosthetic hand if the user settles on the prosthetic foot or on the prosthetic hand.

The exoskeletal structure can have a tubular shape. Tubular shape refers to a cylindrical shape that cross-sections having a variable shape and size can have. The tubular shape can also be curved and thus mostly follow a non-straight axis. The exoskeletal structure shown in FIG. 15 thus has a cross-section of shape and size which is different at a calf level and at an ankle level. The tubular-shaped exoskeletal structure could also be curved and thus follow a socket (29*b*) which has an angle in relation to the prosthesis (12*b*). An exoskeletal structure which has a leg or arm shape thus has a tubular shape.

Figure 16:
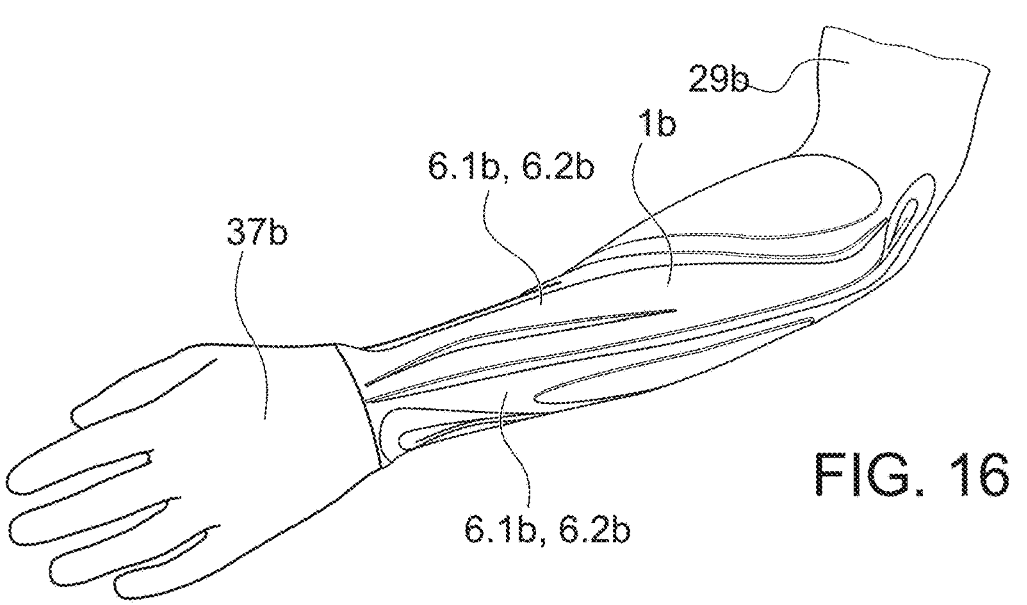
FIG. 16 shows a second example of a prosthesis comprising an exoskeletal structure.
Figure 18:
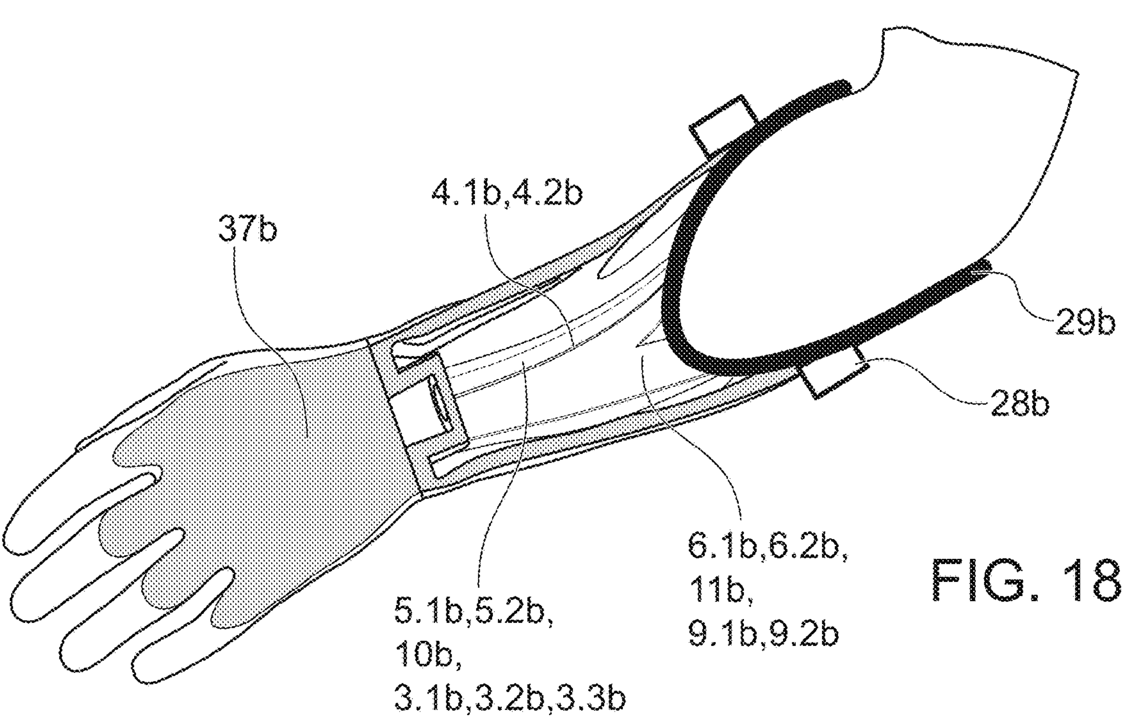
FIG. 18 shows a longitudinal sectional view of a prosthesis according to the second example comprising an exoskeletal structure.
Figure 19:
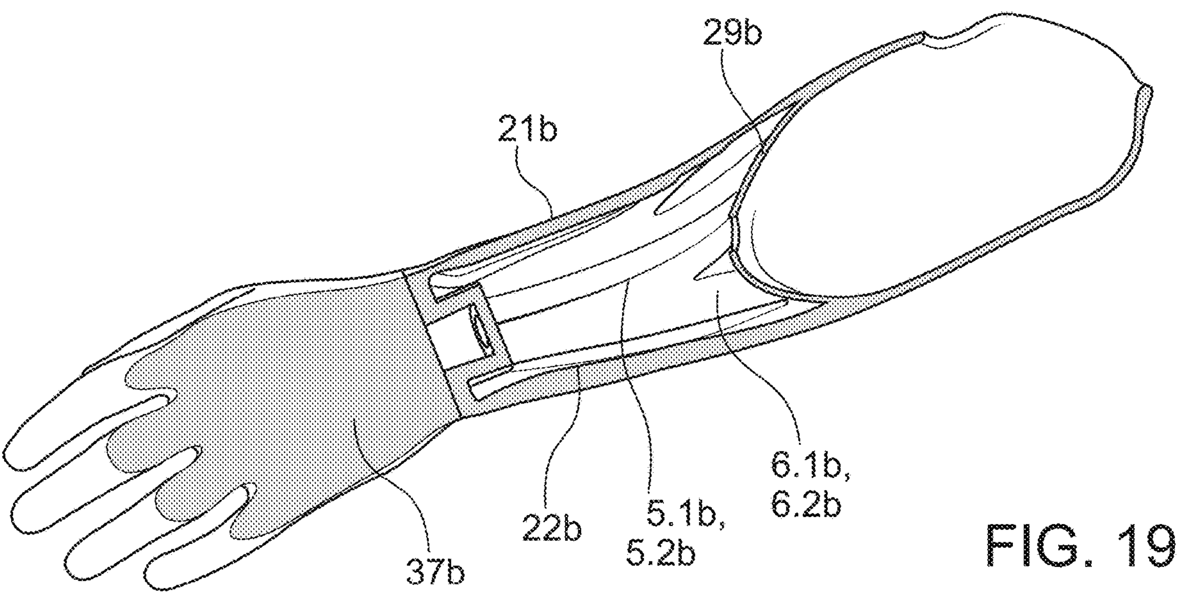
FIG. 19 shows a longitudinal sectional view of a prosthesis according to a third example comprising an exoskeletal structure.

FIGS. 15, 18 and 19 show an inner surface (22*b*) and an outer surface (21*b*) of the exoskeletal structure. The thickness of the exoskeletal structure is a quantity of material between said inner surface and outer surface of the exoskeletal structure. In FIGS. 11, 13 and 16, a first thickness (3.1*b*, 3.2*b*, 3.3*b*) of the exoskeletal structure, a second thickness (9.1*b*, 9.2*b*) and a change of thickness (4.1*b*, 4.2*b*) located between the first (3.1*b*, 3.2*b*, 3.3*b*) and the second (9.1*b*, 9.2*b*) thickness are also identified.

The change of thickness thus demarcates a first zone (5.1*b*, 5.2*b*) having the first thickness (3.1*b*, 3.2*b*, 3.3*b*) from a second zone (6.1*b*, 6.2*b*) having the second thickness (9.1*b*, 9.2*b*).

The exoskeletal structure has a flexibility dependent on the thickness thereof. Thus, if the first zone (5.1*b*, 5.2*b*) has a greater thickness than the second zone (6.1*b*, 6.2*b*), the first zone (5.1*b*, 5.2*b*) will have a lesser flexibility than the second zone (6.1*b*, 6.2*b*).

In other words, if the first zone (5.1*b*, 5.2*b*) has a greater thickness than a mean thickness of the exoskeletal structure and if the second zone (6.1*b*, 6.2*b*) has a lesser thickness than a mean thickness of the exoskeletal structure, the first zone (5.1*b*, 5.2*b*) will have a lesser flexibility than the second zone (6.1*b*, 6.2*b*).

Zones of different flexibility can also be obtained with a difference in material. A first zone can be made of a first material, a second zone can be made of a second material. The first material can be less flexible than the second material. Two zones of different flexibilities are thus obtained.

A difference in material can be understood as a difference in chemical composition of the material. Thus, a polymer used can be more flexible if it comprises an added chemical component, for example if it comprises a plasticizer.

A difference in material can be understood as a difference in macroscopic composition. Thus, a second zone can comprise a thermoplastic polyurethane. A first zone can comprise thermoplastic polyurethane and also carbon fibers. Two zones of different flexibility are thus obtained, the first zone having a lesser flexibility than the second zone due to the properties of the carbon fibers.

It is also possible to obtain zones of different flexibility with a difference in three-dimensional pattern impregnated on the zone. For example, a second zone can comprise a thermoplastic polyurethane. A first zone can comprise thermoplastic urethane impregnated with a three-dimensional deformation rendering said zone less flexible.

On touching the exoskeletal structure, the zone of a greater flexibility gives the impression of touching a soft part of a limb whereas the zone of lesser flexibility gives the impression of touching a hard part of a limb.

The exoskeletal structure can also comprise a plurality of zones having different flexibilities. Two, three, four or more zones can be provided, the set of zones having two, three or more different flexibilities. For example, five zones can be provided, the set of five zones having three different flexibilities.

In this way, it is possible to obtain a plurality of different flexibilities. An exoskeletal structure can thus be obtained in which, to the touch, a plurality of different hardnesses are felt. In this way, the exoskeletal structure can even more specifically resemble touching an anatomy of a limb because, when touched more carefully, it is possible to differentiate more than two parts of different hardnesses on the anatomy of a limb. It is also possible to vary a combination of a thickness, a material and/or a three-dimensional structure to obtain zones of different flexibility.

As a general rule, the most flexible zones can correspond to muscle tissue. For an exoskeletal structure of an arm prosthesis, these consist for example of muscles such as the brachioradialis, the wrist flexor group or the radial group. Less flexible zones can correspond to fibrous parts of the arm, for example the tendons of the preceding muscles, finger muscles or wrist ligaments. The even less flexible or hard zones can correspond to bones, for example the radius or the ulna, preferably essentially in the joint zones.

Different thicknesses of the exoskeletal structure can be made by varying a thickness of a material used for manufacturing the exoskeletal structure. It is also possible to use a material comprising several layers and to vary from one position to another the number of layers to arrive at the different thickness of the exoskeletal structure. It is also possible to use layers made of different materials.

The exoskeletal structure provides the connection between the socket (29*b*) and the prosthetic hand (37*b*) or the prosthetic foot (25*b*) and thus enables the transmission of force between the prosthetic hand or foot and the socket.

Advantageously, said connection is mostly provided by the first zone alone. In other words, the transmission of said force is carried out mostly by the first zone alone. The first zone on its own can thus transmit all of said force. This means that the connection between the socket and the prosthetic hand or foot remains provided even if the second zone was fully removed from the exoskeletal structure.

As described above, the first zone can have a lesser flexibility than the second zone. Having a lesser flexibility, the first zone is deformed less under the effect of a given force than a second zone, which has a greater flexibility. In other words, for a given degree of deformation, the first zone can withstand a greater force than the second zone.

In the case where said connection is mostly provided by the first zone alone, the force transmitted during usual use between the socket and the prosthetic hand or foot results in a deformation of an acceptable value of the first zone if the second zone was removed from the exoskeletal structure.

On comparing the exoskeletal structure in FIG. 1 with the anatomy of FIG. 12, it is observed that the arrangement of the zones of different flexibility (5.1*b*, 5.2*b*, 6.1*b*, 6.2*b*) in relation to one another corresponds to the arrangement of the parts of the limb having different hardnesses (13*b*, 14*b*, 17*b*).

It is observed in FIG. 11 that the second zone (6.1*b*) is arranged mostly longitudinally curving downwards. The first zone (5.1*b*) is arranged so as to widen from a top to a bottom.

The first zone (5.1*b*) is thus arranged in relation to the second zone (6.1*b*) on the exoskeletal structure like the tibia (13*b*) is arranged in relation to the tibialis anterior (14*b*).

The same arrangement of the zones of different flexibility in relation to one another is observed on comparing the exoskeletal structure of an arm prosthesis (FIG. 16) with the anatomy of an arm (FIG. 17).

The arrangement of the zones varies from one patient to another, as the position of the bones, muscles and tendons varies from one patient to another.

In the present example, the first zone (5.1*b*) has a greater thickness than the second zone (6.1*b*). Said first zone thus gives to the touch the impression of being harder than the second zone. The second zone gives the impression of being softer than the first zone.

On touching the exoskeletal structure, the user thus receives a similar sensation to touching a lower part of a human leg or arm. In the case of a leg prosthesis, the first zone (5.1*b*) will feel like touching the tibia and the second zone like touching the tibialis anterior muscle. On sliding a finger between the first zone (5.1*b*) and the second zone (6.1*b*), the change of flexibility, induced by the change of thickness of the exoskeletal structure, is perceived as a change of firmness, between a soft part and a hard part of a human leg or a human arm.

Similarly, it is observed in FIGS. 13 and 14 that a second zone (6.2*b*) having a lesser thickness is arranged on the exoskeletal structure like the fibularis longus (17*b*) on the tibial part of a leg.

A change of thickness to demarcate zones of different flexibility can also be obtained with a rib or with a recess on the exoskeletal structure.

FIG. 13 and FIG. 18 show a rib (10*b*) on the exoskeletal structure to obtain a lesser flexibility at the position where the rib is located. The figures also show a recess (11*b*) to an increased flexibility at the position where the recess is located.

A rib or a recess has a change of thickness of the exoskeletal structure. An exoskeletal structure having a rib comprises a first zone and a second zone having different thicknesses. For example, the zone of the rib itself can be identified as the first zone of greater thickness. The second zone of lesser thickness in relation to the first zone is, in this case, the zone which is located outside the area of the rib.

A use of ribs and recesses enables a particularly fine arrangement of zones of different flexibility.

Advantageously, the exoskeletal structure comprises a thermoplastic polyurethane (TPU) and/or a polyamide.

The thermoplastic polyurethane has advantages for manufacturing an exoskeletal structure of a prosthesis. It enables a good emulation of a contralateral limb, this material can be placed in water and can be washed easily. Under the effect of a shock, the exoskeletal structure comprising this material is deformed and makes no noise. Due to the elasticity and flexibility properties thereof, TPU is particularly suitable for the manufacture of zones of different flexibility to emulate a physiological touch. An exoskeletal structure comprising this material is light and does not add excessive weight to the prosthesis.

The exoskeletal structure can be manufactured using a 3D printing method, for example by powder melting.

The first zone (5.1*b*, 5.2*b*) and the second zone (6.1*b*, 6.2*b*) can have a longitudinal shape (FIG. 11, 12) on the exoskeletal structure, the longitudinal shape extending along an extension of the limb.

In the embodiment example shown in FIGS. 11, 13, 15, 16, 18, 19, 20 and 21, the exoskeletal structure has a tubular shape. The first thickness (3.1*b*, 3.2*b*, 3.3*b*) and the second thickness (9.1*b*, 9.2*b*) remain mostly constant along a length of the exoskeletal structure. The thickness shows a change mostly along a circumference of the tubular shape of the exoskeletal structure.

In the specific case of ribs or recesses, said ribs and recesses extend mostly along a length of the tubular shape.

An arrangement as described above corresponds particularly well for the manufacture of an exoskeletal structure of a prosthesis for an arm or for a leg.

The muscles, tendons and bones of the arm and the leg extend mostly along a length of the arm or the leg. For this reason, on touching an arm or a leg, minor changes in hardness are felt along the limb. A rib or a recess provided along a length of the tubular shape induces a change in hardness felt if a user moves their finger along the circumference of the exoskeletal structure, the hardness remaining constant along the length of the tubular shape. To the touch, the exoskeletal structure thus reproduces a similar behavior to a leg or an arm. Very advantageously, the first zone of the exoskeletal structure, which induces the impression of hardness, similar to a bone, also provides stability to the prosthesis, like a bone does in a natural arm. As a bone provides the connection between the hand and an upper part of the arm, the first zone mostly provides the connection between the hand or foot prosthesis and the socket, which rests on a stump of the limb.

FIGS. 15, 18 and 19 show a leg prosthesis and an arm prosthesis. The prosthesis comprises a prosthetic foot (25*b*) or a prosthetic hand (37*b*) and a socket (29*b*). The exoskeletal structure (1*b*) is located between the socket (29*b*) and the prosthetic foot (25*b*) or the prosthetic hand (37*b*) and thus provides a connection in order to form the leg or arm prosthesis.

It is also noted that no other support element, other than said exoskeletal structure, is provided between the socket and the prosthetic foot or prosthetic hand. Thus, the exoskeletal structure alone provides a connection between the socket and the prosthetic foot or prosthetic hand. The exoskeletal structure alone transmits force between the prosthetic hand or prosthetic foot and the socket. Advantageously, the first zone of the exoskeletal structure provides alone, mostly, said connection without any other support element provided inside the exoskeletal structure.

The exoskeletal structure has a tubular shape (3*b*) comprising an inner surface (22*b*) and an outer surface (21*b*). Advantageously, the outer surface (21*b*) of the exoskeletal structure is mostly smooth in relation to the changes (4.1*b*, 4.2*b*) demarcating the zones of different flexibility.

The expansion or contraction of the material which forms a greater thickness (for example a rib) or lesser thickness (for example a recess) takes place towards an interior of the exoskeletal structure (FIG. 15). The surface remains, in this way, smooth.

More specifically, the inner surface (22*b*) moves away from or closer to the outer surface (21*b*) to induce a change of the thickness. The whole of the outer surface and the inner surface, forming a wall of the exoskeletal structure, can mold a shape resembling an anatomy of a limb. It is observed, for example in FIG. 15, that the wall between the outer surface (21*b*) and the inner surface (22*b*) curves from a top to a bottom to make the exoskeletal structure resemble, at this position, a calf. It is also noted in FIG. 16 that the diameter of the exoskeletal structure first decreases, on moving away from a wrist position, then adopts an arched shape to emulate a shape of a muscle, before ending towards an elbow position. A smooth outer surface means that the inner surface, while following the shape of the outer surface, moves away from and closer to the outer surface to form zones of different thickness. In the specific case of ribs (10*b*) and/or recesses (11*b*), mostly smooth means that the rib and/or the recess is located inside the exoskeletal structure.

The exoskeletal structure imparts by the smooth exterior thereof furthermore a physiological touch, corresponding to smooth skin having different hardnesses to the touch.

It is also possible to provide a mostly smooth inner surface and to locate changes (4.1*b*, 4.2*b*) on an outer surface. Thus, the ribs and/or the recesses can be oriented towards an outer surface.

In addition, the changes (4.1*b*, 4.2*b*) can be located on the outer surface and on the inner surface.

According to a first embodiment, the exoskeletal structure (1*b*), the socket (29*b*) and the foot prosthesis (25*b*) or hand prosthesis (37*b*) are provided in three separate parts. In this case, the foot or hand prosthesis is attached by a first side of the exoskeletal structure. The exoskeletal structure is attached by a second side to the socket. FIGS. 15 and 18 show an exoskeletal structure (1*b*), a foot or hand prosthesis and a socket provided in three separate parts. The exoskeletal structure can be attached to the socket by a gripping collet (28*b*). The gripping collet attaches the exoskeletal structure (1*b*) to the prosthesis socket (29*b*).

Figure 20:
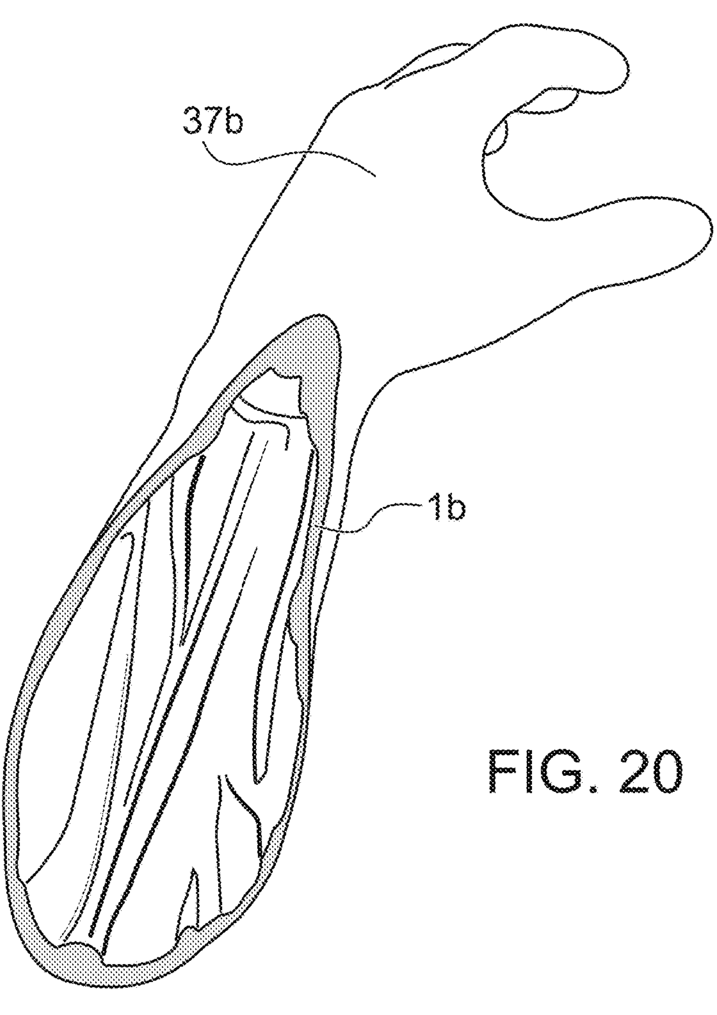
FIG. 20 shows a sectional view of a prosthesis according to a fourth example comprising an exoskeletal structure.

According to a second embodiment, the exoskeletal structure can be integral with the foot prosthesis or hand prosthesis. According to this embodiment, the exoskeletal structure forms a continuous material element with the foot or hand prosthesis. FIG. 20 shows an exoskeletal structure formed of a single continuous material element with the hand prosthesis.

According to a third embodiment, the exoskeletal structure can be integral with the socket. The exoskeletal structure thus forms a continuous material element with the socket. FIG. 19 shows an exoskeletal structure integral with a socket (29*b*), forming a single continuous material element.

According to a fourth embodiment, the exoskeletal structure, the hand prosthesis or foot prosthesis and the socket can all be integral together to form a continuous material element. The exoskeletal structure, the hand prosthesis or foot prosthesis and the socket form in this way a single continuous material element.

The exoskeletal structure, the socket and the foot or hand prosthesis described above can be manufactured advantageously with the method described hereinafter.

In a first step, a three-dimensional image of a limb is obtained.

For example, a patient's non-amputated limb is digitized using a 3D scanner to obtain said image. Via said image, a representation of the surface of this limb is obtained, i.e. a three-dimensional digital representation of the limb is obtained. The digital representation of the limb is a three-dimensional surface.

Alternatively, a three-dimensional image obtained from a data library could be used. In this case, said image is obtained from a library of morphotypes based on the patient's height and weight.

A scanned image of the patient's limb obtained before the limb was amputated could also be used.

In the present example, a digital representation of a tibial part of a leg is obtained, i.e., a digital representation of a lower part of the leg as shown in FIGS. 12 and 14 for a leg prosthesis. For a lower arm prosthesis, a digital representation of the lower arm is obtained, i.e., a digital representation of a part as shown in FIG. 17 below.

Similarly, a digital representation of a foot can also be obtained. As described above, it is possible to use a 3D scanner or to retrieve an image from an image library.

Similarly, a digital representation of a leg with its foot can be obtained, using a 3D scanner or by retrieving an image from an image library.

Similarly, a digital representation of a hand, an arm with its hand, or an arm and a hand separately can also be obtained.

In a second step, the parts of the limb having different hardnesses (7*b*, 8*b*) are identified on the digital representation of the limb. This identification can be made automatically, manually by an operator or by an operator assisted by an algorithm. This identification can be made on the complete digital representation or only on a part of the digital representation. In the example of a digital representation of a leg with its foot, this identification can be made, for example, only on the part of the leg excluding the foot. Following this step, a demarcation of the parts having different hardnesses can be plotted on the representation of the limb. In other words, an arrangement of the parts of different hardness in relation to one another can be plotted on the representation of the limb.

For example, on a digital representation of a tibial part of a leg, the part corresponding to the tibia and the part corresponding to the tibialis anterior are identified. Then, on the digital representation, a line is plotted to demarcate an extension of the tibia and the tibialis anterior under the skin. For example, on a digital representation of an arm, the part corresponding to the ulna and the part corresponding to the flexor are identified. Then, on the digital representation, a line is plotted to demarcate an extension of the ulna and the flexor under the skin.

Advantageously, the first zone which will mostly provide the connection provided by the exoskeletal structure between the socket and the hand or foot prosthesis is also demarcated. For example, on the digital representation, a zone similar to the position of the tibia or the ulna is plotted, which will be the first zone on the exoskeletal structure for transmitting force between the socket and the hand or foot prosthesis, in order to provide said connection.

In a third step, the exoskeletal structure is designed. The exoskeletal structure is designed, according to the embodiment integral with the socket and/or the foot or hand prosthesis or separately. The second and the third step can be carried out using computer-aided design (CAD) software.

On a digital model of the exoskeletal structure, a zone is defined by defining the shape thereof. A zone shape is then plotted on the surface of the exoskeletal structure. Then, a flexibility of this zone is defined. For example, the thickness that the material of the exoskeletal structure will have in this zone is set. At the end of this step, an arrangement of zones of different flexibilities, for example obtained with different thicknesses, is defined on the exoskeletal structure. Advantageously, the first zone is defined in order to be able to provide mostly the connection between the socket and the foot and hand prosthesis alone. The shape of the first zone and/or the thickness of the first zone and/or the material of the first zone is or are thus chosen so that the first zone can transmit a required force between the socket and the hand or foot prosthesis. The required force is dependent on an intended use. The required force can be, for example, greater for a leg prosthesis than for an arm prosthesis, greater for an adult's prosthesis than for a child's prosthesis and greater for a prosthesis for a patient having a high body weight than for a light patient. The material and/or thickness and/or structure and/or a reinforcement and/or the geometric shape will thus be chosen so that the first zone can transmit the required force on its own, i.e., without a presence of other zones.

The shape and flexibility of the zones are defined so as to correspond to the arrangement of the parts of the limb having different hardnesses.

In an example using different thicknesses, on the exoskeletal structure, a first zone having a greater thickness will be located in relation to a second zone having a lesser thickness as a harder part of the limb is located in relation to a softer part on the digital representation of the limb, said parts being identified previously as described above.

To verify the arrangement of said zones in relation to one another and the correspondence to the arrangement of the parts of the limb, the digital representation of the exoskeletal structure for a prosthesis can be projected on the digital representation of the limb.

In this way, a zone having a greater thickness than a mean thickness is arranged to coincide with a hard part of the limb and/or a zone having a lesser thickness than a mean thickness is arranged to coincide with a soft part of the limb.

For example, on a digital model of the exoskeletal structure as seen in FIG. 11, a first zone (5.1*b*) corresponding by the shape thereof to the tibia part (13*b*) is plotted. The tibia part has been previously identified on the digital representation of the leg.

Then, a second zone (6.1*b*) is plotted on the digital model of the exoskeletal structure corresponding by the shape thereof to the tibialis anterior part (14*b*), as previously identified on the digital representation of the leg.

Then, a greater thickness is associated with the first zone and a lesser thickness with the second zone.

The exoskeletal structure manufactured will thus be less flexible at the first zone than at the second zone, like a leg is harder at a part corresponding to the tibia and softer at a part corresponding to the tibialis anterior. The exoskeletal structure imparts in this way a physiological touch for a user.

It is also possible to give the exoskeletal structure the shape of the limb as deduced from the digital representation of the original limb. The exoskeletal structure adopts, in this way, the shape of the limb. The exoskeletal structure can thus adopt the three-dimensional shape of the leg, for example of the tibial part or of the arm, for example of the forearm. Furthermore, the prosthetic foot can adopt the shape of the foot as identified on the digital representation and the prosthetic hand can adopt the shape of the hand as identified on the digital representation.

An exoskeletal structure which adopts the shape of the limb and imparts at the same time a physiological touch is particularly suitable for giving a user a natural feeling when wearing their prosthesis.

The exoskeletal structure can then be manufactured using a 3D printing method from the digital model. More specifically, powder melt 3D printing can be used, for example with TPU.

It is thus possible to manufacture an exoskeletal structure for a leg prosthesis or for an arm prosthesis.

In the case of a leg prosthesis, the exoskeletal structure comprising the leg prosthesis can be manufactured using a digital representation of a complete leg with its foot, with the method described above. In this case, it is possible to manufacture the prosthesis comprising the prosthetic foot. The exoskeletal structure for the leg prosthesis and the foot prosthesis can be manufactured in two separate parts. The exoskeletal structure for the leg prosthesis and the foot prosthesis can also be manufactured integral with one another. In the latter case, a prosthesis made of a single continuous material element comprising the foot prosthesis and the exoskeletal structure made of a single continuous material element is obtained. In other words, using a digital representation of a complete leg with its foot, the leg prosthesis comprising the foot prosthesis can be manufactured with a single continuous material element. It is possible to impart on this prosthesis the shape as defined by the digital representation. In other words, the exoskeletal structure reproduces the shape of the leg at a calf level according to the digital representation and the foot prosthesis reproduces the shape of the foot according to the digital representation. In summary, a complete prosthesis, including a tibial part with a foot prosthesis, can be obtained using a representation of a complete leg with its foot. This prosthesis can have the shape of the complete leg with its foot, and impart, in places or completely, a physiological touch.

Similarly, an upper limb prosthesis, for example of an arm, can be obtained. In the case of an arm prosthesis, the prosthesis can also be manufactured using a digital representation of a complete arm with its hand, with the method described above. The exoskeletal structure for the arm prosthesis and the hand prosthesis can be manufactured in two separate parts or integral with one another. In other words, it is possible to manufacture using a digital representation of the complete arm with its hand the exoskeletal structure and the hand prosthesis with a single continuous material element. The exoskeletal structure and/or the hand prosthesis can adopt the shape as defined by the digital representation of the arm with or without its hand.

Figure 21:
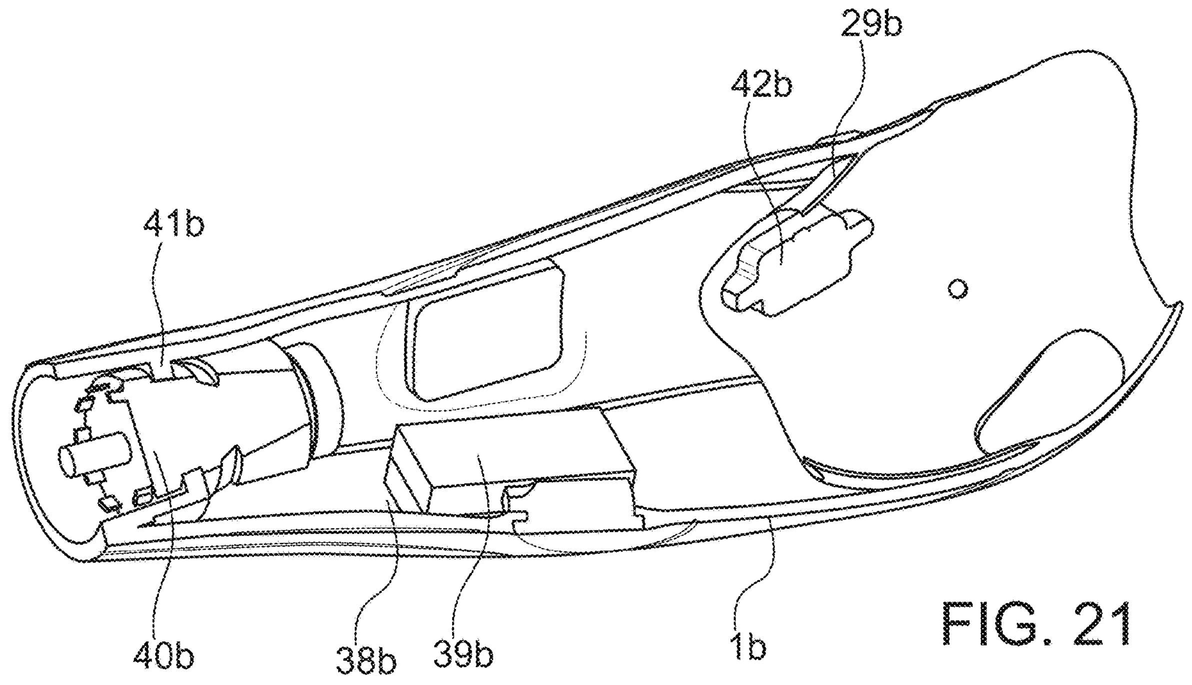
FIG. 21 shows a sectional view of an exoskeletal structure of a prosthesis according to a fifth example.

FIG. 21 shows an exoskeletal structure of a prosthesis (1*b*), a socket (29*b*), an electronic component (39*b*) and an electronic component attachment device (38*b*). FIG. 21 also shows a motor (40*b*) and a motor attachment device (41*b*) and a sensor (42*b*). The electronic component is attached inside the exoskeletal structure by the attachment device (38*b*). The motor is attached on a side opposite the socket by the motor attachment device. The sensor (42*b*) is attached inside the socket in order to be able to come into contact with a user's stump.

In the present example, the socket is integral with the exoskeletal structure. The exoskeletal structure comprising the attachment device can be designed and manufactured with the method described above. In this case, the method can comprise a step during which the location of the attachment device is determined, preferably so as to prevent an influence on the physiological touch imparted by the exoskeletal structure.

The exoskeletal structure shown in FIG. 21 is particularly suitable for forming a myoelectric prosthesis. Myoelectric prostheses work thanks to muscle contractions controlled by the patient. Advantageously, the sensor (42*b*) is thus a sensor of a myoelectric prosthesis. The sensor (42*b*) receives the muscle signals from the patient's stump. The signals can be amplified and then sent to the motor (41*b*). The motor can start up thanks to power supplied by a battery. The electronic component (39*b*) can, for example, be a battery or a processor designed to manage operating of the motor (40*b*) based on the signals sent by the sensor (42*b*) or an amplifier to amplify the signals received by the sensor (42*b*).

The invention claimed is:

1. A covering shell for a prosthesis of a replaced limb, the covering shell resembling at least parts of the replaced limb and the covering shell comprising at least two zones of different flexibility, an arrangement of said zones in relation to one another coinciding with an arrangement of parts of the replaced limb having different hardnesses, the covering shell resembling through different flexibilities thereof different parts of the replaced limb when touched;

wherein a first zone differs from a second zone in relation to at least one of a thickness, a material and a three-dimensional pattern, in order to obtain a first zone having a different flexibility from a second zone;

the covering shell being adapted for housing a leg prosthesis therein; and wherein each zone has at least one of the following:

a greater thickness than a mean thickness of the shell, said each zone located on the shell represents a tibia located under a leg's skin, and a lesser thickness than a mean thickness of the shell, said each zone located on the shell represents a muscle or a tendon located under a leg's skin, the muscle or the tendon being a soleus, a tibialis anterior, a fibularis longus, an extensor digitorum longus, a gastrocnemius or Achille's tendon.

2. The shell according to claim 1, wherein at least one of the following: a first zone has a lesser flexibility than a second zone, the first zone being arranged to coincide with a hard part of the limb, and a second zone has a greater flexibility than a first zone, the second zone being arranged to coincide with a soft part of the limb.

3. The shell according to claim 2, wherein the first zone and the second zone have different thicknesses, and the first zone and the second zone are a rib or a recess.

4. The shell according to claim 1, wherein the shell has a tubular shape capable of receiving said prosthesis inside the tubular shape.

5. The shell according to claim 4, wherein at least one of the following: a flexibility of the shell remains mostly constant along a length of the tubular shape, and the flexibility of the shell mostly changes along a circumference of the tubular shape.

6. The shell according to claim 1, wherein an outer surface of the shell is mostly smooth and the changes in thickness are located on an inner surface of the shell.

7. An assembly of a covering shell for a leg prosthesis and a covering shell for a foot prosthesis, the covering shell being according to claim 1, the covering shell of the leg prosthesis being integral with the covering shell of the foot prosthesis.

8. An assembly of a covering shell for a prosthesis according to claim 1 and a covering shell for a prosthetic foot, the covering shell having a tubular shape and comprising at least one lug on a bottom edge of the tubular shape, the lug being capable of interlocking reversibly in the shell of the prosthetic foot, so as attach it removably to the tubular shape.

* * * * *